United States Patent
Lindsey et al.

(10) Patent No.: US 7,022,862 B2
(45) Date of Patent: Apr. 4, 2006

(54) SCALABLE SYNTHESIS OF DIPYRROMETHANES

(75) Inventors: Jonathan S. Lindsey, Raleigh, NC (US); Savithri Dhanalekshmi, Raleigh, NC (US); Joydev K. Laha, Raleigh, NC (US); Masahiko Taniguchi, Raleigh, NC (US)

(73) Assignee: North Carolina State University, Raleigh, NC (US)

( * ) Notice: Subject to any disclaimer, the term of this patent is extended or adjusted under 35 U.S.C. 154(b) by 389 days.

(21) Appl. No.: 10/641,412

(22) Filed: Aug. 15, 2003

(65) Prior Publication Data

US 2005/0038262 A1     Feb. 17, 2005

(51) Int. Cl.
*C07D 207/30* (2006.01)

(52) U.S. Cl. .................. 548/518; 548/400; 548/517

(58) Field of Classification Search ............. 548/517, 548/518, 400
See application file for complete search history.

(56) References Cited

U.S. PATENT DOCUMENTS

2003/0096978 A1   5/2003   Lindsey et al.

OTHER PUBLICATIONS

U.S. Appl. No. 10/456,421, filed Jun. 6, 2003, Lindsey et al.
Hammel, Dirk, et al., *Synthesis and Reduction of 1,4-Phenylene-Bridged Oligoporphyrins*, Advanced Materials, vol. 4, No. 11, pp. 737-739 (1992).
Littler, Benjamin J., et al., *Refined Synthesis of 5-Substituted Dipyrromethanes*, The Journal of Organic Chemistry, vol. 64, No. 4, pp. 1391-1396 (1999).
Nagarkatti, Jia P., et al., *Synthesis of Pyridyl meso Substituted Dipyrrylmethenes*, Synthesis, pp. 186-187 (Mar. 1974).
Staab, Heinz A., et al., *Synthesis and Properties of New Quinone-Bridged Diphenyl- and Tetraphenylporphyrins*, Chem. Ber., vol. 127, pp. 223-229 (1994).
Vigmond, Stephen J., et al., *Direct Synthesis of Aryldipyrromethanes*, Tetrahedron Letters, vol. 35, No. 16, pp. 2455-2458 (1994).

*Primary Examiner*—Golam M. M. Shameem
(74) *Attorney, Agent, or Firm*—Myers Bigel Sibley & Sajovec, PA

(57) ABSTRACT

A (preferably nonaqueous) method of making a dipyrromethane is described. The comprises the steps of: (a) providing a reaction system consisting essentially of an aldehyde or acetal, excess pyrrole and a catalyst; (b) reacting the aldehyde or acetal with the pyrrole in the reaction system to form the dipyrromethane therein; (c) quenching the reaction system by adding a base thereto (preferably without simultaneously or concurrently adding water and/or an organic solvent thereto); (d) separating the catalyst from the reaction system; and then (e) separating the pyrrole from the reaction system to produce the dipyrromethane as a residual

24 Claims, 5 Drawing Sheets

SCALABLE SYNTHESIS OF DIPYRROMETHANES

STATEMENT OF GOVERNMENT SUPPORT

This invention was made with Government Support under Grant No. GM36238 from the National Institutes of Health. The Government has certain rights to this invention.

FIELD OF THE INVENTION

This invention concerns methods for the synthesis of dipyrromethanes, along with the synthesis of additional products such as porphyrinic macrocycles and dipyrrins therefrom.

BACKGROUND OF THE INVENTION

Dipyrromethanes have occupied a central place in porphyrin chemistry since the time of Hans Fischer. The dipyrromethane structures employed in the synthesis of naturally occurring porphyrins typically bear substituents at the β-positions and lack any substituent at the meso-position (Chart 1). In the past decade, meso-substituted dipyrromethanes lacking any β-substituents have come to play a valuable role in the preparation of synthetic porphyrins and related compounds such as dipyrrins and chlorins. A number of stepwise syntheses of dipyrromethanes lacking β-substituents have been developed,[1] while more direct routes have employed one-flask condensations of pyrrole and the desired aldehyde.

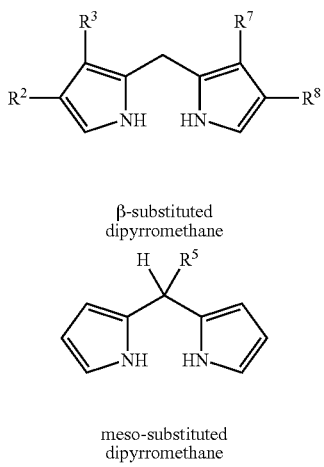

Chart 1

β-substituted dipyrromethane meso-substituted dipyrromethane

The earliest one-flask synthesis entailed reaction of 4-pyridine carboxaldehyde with 2.1 molar equiv of pyrrole in methanol acidified with gaseous HCl, whereupon the corresponding 5-(4-pyridyl)dipyrromethane precipitated as the hydrochloride salt.[2] In most applications such precipitation is not possible, in which case all excess of pyrrole is employed to suppress the continued reaction leading to linear and cyclic oligomers. A number of reports in the early-mid 1990s described methods where the aldehyde (0.04–0.5 M) was treated with excess pyrrole (2.1–40 molar equiv) in an acidified organic solvent: BF[3]-etherate/CH$_2$Cl$_2$,[3] acetic acid/DMF[4] or THF,[5] SnCl$_4$/CH$_2$Cl$_2$,[6] p-toluenesulfonic acid/MeOH[7,8] or toluene,[9] or aq. HCl/THF.[10] Workup typically entailed several steps including column chromatography, though Hammel et al. employed flash chromatography followed by Kugelrohr distillation.[3] In 1994, we reported a method that employed the reaction of the aldehyde (0.34 M) dissolved in neat pyrrole (~14 M) with no other solvent, relying on column chromatography for purification ("1994 procedure").[11] Catalysis was achieved at room temperature with TFA or BF$_3$.O(Et)$_2$, or in some cases[12] upon heating without added acid. The reaction proceeded in a few minutes at room temperature and afforded the dipyrromethane in yields of ~40–60%, but the use of chromatography for purification limited the scale.

Several groups have made modifications to the 1994 procedure. Both Boyle and we altered the workup protocol to facilitate preparative scale synthesis. Boyle employed flash chromatography to remove higher oligomers followed by Kugelrohr distillation, affording as much as ~9 g of product.[13-15] We examined the crude reaction mixture and found the dominant products to consist of the dipyrromethane, N-confused dipyrromethane, tripyrrane and other oligomers.[16] We developed the following purification protocol: (1) aqueous base treatment and extraction with ethyl acetate; (2) removal of ethyl acetate and pyrrole; (3, optional) filtration through a pad of silica to remove high oligomers, which was typically done in cases where the crude products were especially discolored; (4) Kugelrohr distillation to give the dipyrromethane and N-confused dipyrromethane; and (5) recrystallization to remove the N-confused dipyrromethane. While this multistep purification protocol was effective for many aldehydes in small scale preparations, other aldehydes were too large or sensitive for distillation, requiring resort to chromatography. A few reports have appeared of the direct crystallization of the dipyrromethane from the reaction mixture, but given the complexity of the reaction mixture, direct crystallization appears to be viable only for selected aldehydes.[17]

We sought to modify the conditions of the 1994 procedure such that the dipyrromethane could be isolated by crystallization from the crude reaction mixture. Our approach was guided by several observations. (1) Our prior analysis of the product distribution of the dipyrromethane-forming reaction employed GC and quantitated only the volatile products (dipyrromethane, N-confused dipyrromethane, and tripyrrane; ~80%, 2–3%, and 15%, respectively, with TFA catalysis) of the reaction.[16] However, TLC analysis of the crude reaction mixture showed the presence of "black material" at the origin, which was not analyzed by GC. Accordingly, the isolated yield of dipyrromethane generally fell significantly below the expected 85%. (2) We recently found that a wide variety of acid catalysts can be used in the pyrrole-aldehyde condensation leading to the porphyrinogen.[18,19] We also found that several mild Lewis acids [InCl$_3$, Sc(OTf)$_3$, Dy(OTf)$_3$, Yb(OTf)$_3$] afford superior results compared with TFA in porphyrin syntheses via dipyrromethane-carbinols.[20,21] Mild Lewis acids of this type have been found to have beneficial effects in diverse synthetic reactions.[22] (3) In a few cases examined, a larger pyrrole:aldehyde ratio (e.g., 400:1) gave dipyrromethanes in yields of 90–95%.[21,23] Accordingly, we began our studies by examining acids and pyrrole:aldehyde ratios that might afford less black material, which consumes starting material and complicates the purification procedure.

During the course of our work, two new methods were reported for carrying out the aldehyde-pyrrole condensation leading to dipyrromethanes: the use of ion exchange resins as acid catalysts,[24] and the use of refluxing aqueous acid as a solvent for the reaction from which the dipyrromethane is obtained as a crystalline solid.[25] The one-flask solventless synthesis approach also has found other applications, including (1) reaction of an aldehyde with excess furan or thiophene affording the difurylmethane or dithienylmethane, respectively;[26] (2) reaction of excess pyrrole with a ketone affording a 5,5-dialkyldipyrromethane;[27] and (3) reaction of excess pyrrole with an orthoester affording the corresponding tripyrromethane.[28] Such reports illustrate the ongoing interest in efficient one-flask syntheses of dipyrromethanes.

SUMMARY OF THE INVENTION

The present invention provides a method of making a dipyrromethane. The method is preferably and advantageously a non-aqueous method (that is, carried out with a non-aqueous reaction system throughout), and is preferably and advantageously carried out without the addition of further organic solvents during separating steps. In general, the method comprises the steps of: (a) providing a reaction system consisting essentially of an aldehyde or acetal, excess pyrrole and a catalyst; (b) reacting the aldehyde or acetal with the pyrrole in the reaction system to form the dipyrromethane therein; (c) quenching the reaction system by adding a base thereto (preferably without simultaneously or concurrently adding water and/or an organic solvent thereto); (d) separating the catalyst from the reaction system (preferably by a filtration or a gravity technique such as centrifugation and settling/decanting); and then (e) separating the pyrrole from the reaction system to produce the dipyrromethane as a residual. The method may optionally include the further step of (f) crystallizing the dipyrromethane.

In some embodiments, the method may further comprise the step of synthesizing a porphyrinic macrocyle from the dipyrromethane (e.g., by reaction of a dipyrromethane and an aldehyde, or reaction of a dipyrromethane and a dipyrromethane-dicarbinol).

In some embodiments, the method may further comprise the step of synthesizing a dipyrrin from the dipyrromethane.

The present invention is explained in greater detail in the drawings herein and the specification set forth below.

DETAILED DESCRIPTION OF THE PREFERRED EMBODIMENTS

Figure 1:
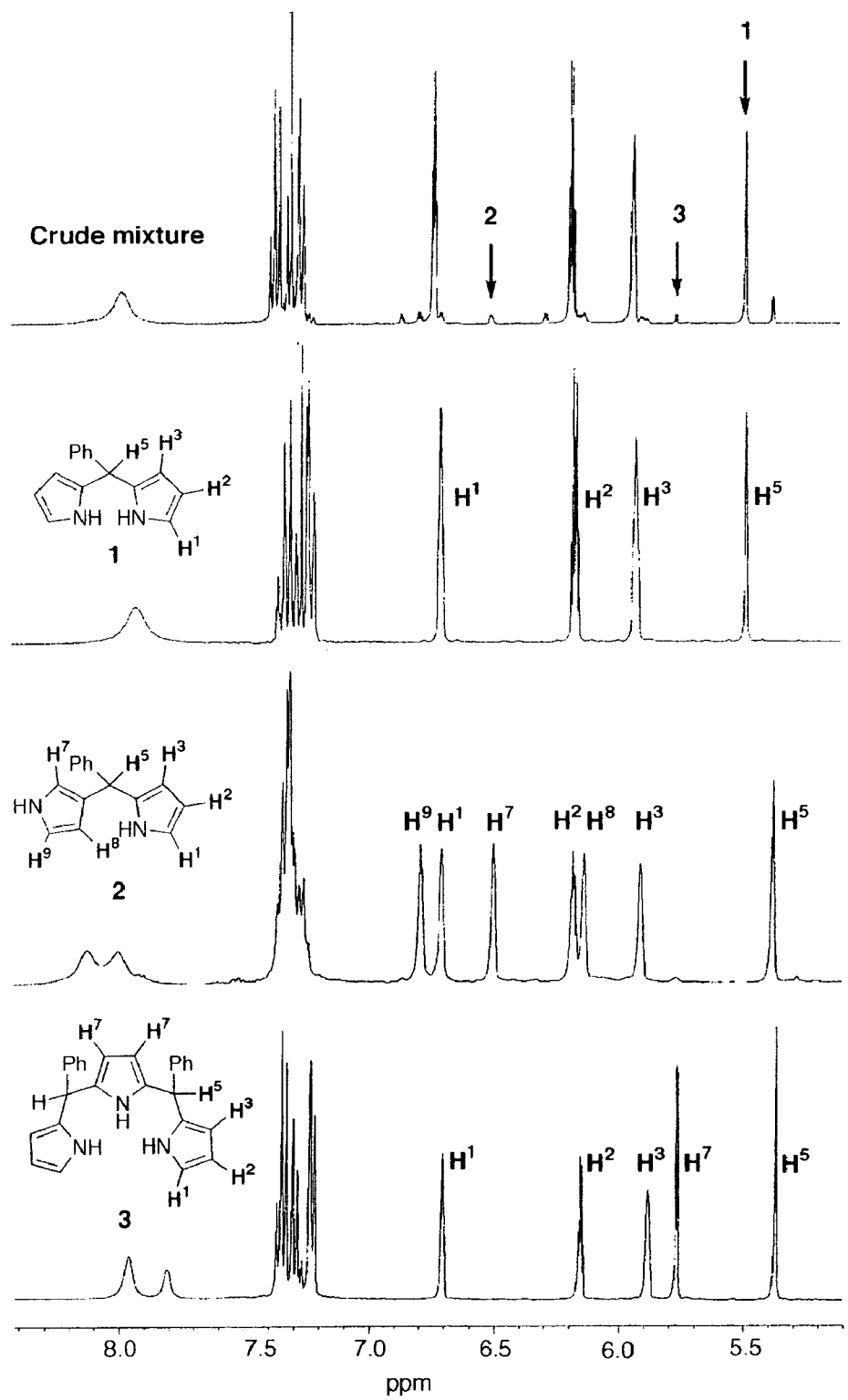
FIG. 1. $^1$H NMR spectra (in $CDCl_3$, 400 MHz) of 5-phenyldipyrromethane (1), N-confused 5-phenyldipyrromethane (2), 5,10-diphenyltripyrrane (3) and a sample from the crude reaction mixture (following neutralization and removal of pyrrole) obtained from the condensation of pyrrole and benzaldehyde (100:1) using 0.1 equiv of $InCl_3$. All the pyrrole protons were assigned by 2D $^1$H NMR.

The term "porphyrinic macrocycle" or "porphyrin macrocycle" as used herein refers to a porphyrin or porphyrin derivative. Such derivatives include porphyrins with extra rings ortho-fused, or orthoperifused, to the porphyrin nucleus, porphyrins having a replacement of one or more carbon atoms of the porphyrin ring by an atom of another element (skeletal replacement), derivatives having a replacement of an atom of the porphyrin ring by an atom of another element (skeletal replacement), derivatives having substituents other than hydrogen located at the peripheral (meso-, β-) or core atoms of the porphyrin, derivatives with saturation of one or more bonds of the porphyrin (hydroporphyrins, e.g., chlorins, bacteriochlorins, isobacteriochlorins, decahydroporphyrins, corphins, pyrrocorphins, etc.), derivatives obtained by coordination of one or more metals to one or more porphyrin atoms (metalloporphyrins), derivatives having one or more atoms, including pyrrolic and pyrromethenyl units, inserted in the porphyrin ring (expanded porphyrins), derivatives having one or more groups removed from the porphyrin ring (contracted porphyrins, e.g., corrin, corrole) and combinations of the foregoing derivatives (e.g. phthalocyanines, porphyrazines, naphthalocyanines, subphthalocyanines, and porphyrin isomers). Preferred porphyrinic macrocycles comprise at least one 5-membered ring.

"Dipyrrin" (also known as dipyrromethene) or "dipyrrin group" as used herein includes unsubstituted or substituted dipyrrins, which may be substituted one or more times at the 1, 2, 3, 5, 7, 8 or 9 positions with any suitable substituent such as halo, carbonyl, alkyl fluoroalkyl including perfluoroalkyl, ail (e.g., aryl at the 5 position; alkyl at the 1 and/or 9 position), fluoroaryl including perfluoroaryl, etc. Dipyrrins may be coupled to porphyrinic macrocycles at any suitable position on the dipyrrin, including the 1, 2, 3, 5, 7, 8, or 9 position.

"Dipyrromethane" as used herein includes unsubstituted or substituted dipyrromethane, which may be substituted one or more times at the 1, 2, 3, 5, 7, 8 or 9 positions with any suitable substituent such as halo, carbonyl, alkyl, fluoroalkyl including perfluoroalkyl, aryl (e.g., aryl at the 5 position; alkyl at the 1 and/or 9 position), fluoroaryl including perfluoroaryl, etc. Dipyrromethanes may be coupled to porphyrinic macrocycles at any suitable position on the dipyrromethanes, including the 1, 2, 3, 5, 7, 8, or 9 position.

"Non-aqueous" as used herein refers to a material or composition to which water has not been added. A non-aqueous composition may contain trace amounts of water (e.g., up to 0.1, 1 or 2 percent by weight, or may be dried so that all water is removed (i.e., anhydrous). Non-aqueous compositions of the invention may contain water that although not added to the composition as exogenous water, is formed in the composition as a reaction product in the course of the reactions described herein.

Bis(dipyrrinato)metal and metal-dipyrrin are terms used interchangeably herein, and are sometimes symbolized as "(dp)$_2$M" or "M(dp)$_2$".

The term "alkyl," as used herein, refers to a straight or branched chain hydrocarbon containing from 1 to 10 carbon atoms. Representative examples of alkyl include, but are not limited to, methyl, ethyl, n-propyl, iso-propyl, n-butyl, sec-butyl, iso-butyl, tert-butyl, n-pentyl, isopentyl, neopentyl, n-hexyl, 3-methylhexyl, 2,2-dimethylpentyl, 2,3-dimethylpentyl, n-heptyl, n-octyl, n-nonyl, n-decyl, and the like, which may be substituted or unsubstituted.

The term "aryl," as used herein, refers to a monocyclic carbocyclic ring system or a bicyclic carbocyclic fused ring system having one or more aromatic rings. Representative examples of aryl include, azulenyl, indanyl, indenyl, naphthyl, phenyl, tetrahydronaphthyl, and the like, which may in turn be substituted or unsubstituted.

"Neutral conditions" as used herein refers to reaction conditions in which a Bronsted acid or an effective amount of a Bronsted acid is absent from the solvent or solvent system in which a reaction is carried out.

"Bronsted acid" as used herein refers to a molecular entity (and corresponding chemical species) that is a proton donor to a base. Any suitable Bronsted acid may be used as a catalyst, with examples including but not limited to: trifluoroacetic acid, trichloroacetic acid, oxalic acid, taurine, malonic acid, formic acid, acetic acid, and NH$_4$Cl.

"Lewis acid" as used herein refers to a molecular entity (and corresponding chemical species) that is an electron-pair acceptor and therefore able to react with a Lewis base to form a Lewis adduct, by sharing the electron pair furnished by the Lewis base. Any suitable Lewis acid may be used as a catalyst, examples including compounds of the general formula LnX$_3$ where Ln is a lanthanide and X is halo such as Cl, Br, I, etc., triflate or OTf, etc, and with examples specific examples including but not limited to: Yb(OTf)$_3$, InCl$_3$, Sc(OTf)$_3$, MgBr$_2$ and CeCl$_3$.

"Aldehyde" as used herein refers to a compound of the formula RC(=O)H, in which a carbonyl group is bonded to one hydrogen atom and to an R group. Any suitable organic R group, or hydrogen as an R group, may be used in the aldehyde, including aliphatic (e.g. alkyl) and aromatic or aryl R groups (all of which may be substituted or unsubstituted), with particular examples including porphyrin, dipyrrin, and diacyldipyrromethane R groups (all of which may be substituted or unsubstituted). Examples of particular aldehydes that may be used include but are not limited to: formaldehyde, paraformaldehyde, acetaldehyde, propionaldehyde, n-butyraldehyde, benzaldehyde, p-nitrobenzaldehyde, p-tolualdehyde, salicylaldehyde, phenylacetaldehyde, α-methylvaleraldehyde, β-methylvaleraldehyde, γ-methylvaleraldehyde, 4-pyridine carboxaldehyde, pentafluorobenzaldehyde, 4-ethynylbenzaldehyde, 4-[2-(triisopropylsilyl)ethynyl]benzaldehyde, 4-[3-methyl-3-hydroxy-but-1-ynyl)benzaldehyde, 4-(S-acetylthiomethyl)benzaldehyde, 4-(Se-acetyl-selenomethyl)benzaldehyde, 4-(hydroxymethyl)benzaldehyde, 4-vinylbenzaldehyde, 4-allylbenzaldehyde, 4-cyanobenzaldehyde, 4-iodobenzaldehyde, 4-(bromomethyl)benzaldehyde, 4-(2-bromoethyl)benzaldehyde, 4-(1,3-dithiolan-2-yl)benzaldehyde, 4-(1,3-dithian-2-yl)benzaldehyde, 4-(4,4,5,5-tetramethyl-1,3,2-dioxaborolan-2-yl)benzaldehyde, 4-(acetoxymethyl)benzaldehyde, 4-[2-(trimethylsilyl)ethoxy-carbonyl]benzaldehyde, 4-methoxycarbonylbenzaldehyde, 5-[4-(di-tert-butyloxyphosphoryl)benzaldehyde, 5-[4-(diethoxyphosphoryl)benzaldehyde, 5-[4-(di-tert-butyloxyphosphorylmethyl)benzaldehyde, 5-[4-(diethoxyphosphorylmethyl)benzaldehyde, 1,1,1-tris[4-(diethoxyphosphorylmethyl)phenyl]-1-(4-formylphenyl)methane, 1,1,1-tris[4-(S-acetylthiomethyl)phenyl]-1-(4-formylphenyl)methane, 3-(S-acetylthiomethyl)benzaldehyde, 3,5-diethynylbenzaldehyde, 3,5-bis[2-(triisopropyl-silyl)ethynyl]benzaldehyde, 4-(5,10,15-tri-p-tolylporphinatozinc(II)-20-yl)benzaldehyde, 4-(5,10,15-tri-p-tolylporphin-20-yl)benzaldehyde, 4-(dipyrrin-5-yl)benzaldehyde, 4-[1,9-bis(4-methylbenzoyl)dipyrromethan-5-yl]benzaldehyde, 4-ferrocenylbenzaldehyde, propargyl aldehyde, bromomethylpropargyl aldehyde, chloromethylpropargyl aldehyde, S-acetylthiomethylpropargyl aldehyde, 4-(hydroxymethyl)phenylpropargyl aldehyde, hydroxyacetaldehyde, and pyruvic aldehyde.

"Acetal" as used herein refers to compounds known as "latent aldehydes" that produce the same products as can be produced with an aldehyde as described above in reactions of the present invention. Acetals are in general compounds of the general formula RC(—OR')(—OR")H, wherein R is as given above and R' and R" are any suitable organic substituent such as alkyl or aryl (e.g. methyl, ethyl, propyl, butyl, phenyl).

Applicants specifically intend the disclosures of all US patent references cited herein to be incorporated by reference herein in their entirety.

As noted above, the present invention provides a method of making a dipyrromethane. The method is preferably and advantageously a non-aqueous method (that is, carried out with a non-aqueous reaction system throughout), and is preferably and advantageously carried out without the addition of further organic solvents during separating steps. While the invention is described with respect to the preferred non-aqueous embodiment below, it will however be appreciated that in some embodiments the advantages of the present invention can also be realized, at least in part, with reaction systems that contain some water at lesser amounts (e.g., reaction systems that contain not more than 5 or 10 percent by weight water at the various steps of the process described herein.

The method first comprises the step of (a) providing a reaction system comprising, consisting of or consisting essentially of an aldehyde or acetal, excess pyrrole and a catalyst. The amount of the aldehyde or acetal in the reaction system will vary depending upon the particular aldehyde or acetal used, but in general the molar ratio of the pyrrole to the aldehyde or acetal is 50:1 to 5,000:1. Stated differently, in general the amount of aldehyde or acetal is from 0.05 or 0.5 to 1 or 5 percent by weight of the system, or more, and the amount of pyrrole in the system is generally from 95 or 98 to 99 or 99.9 percent by weight of the system, or more. The catalyst may be a Bronsted acid or a Lewis acid, and the amount of catalyst in the system is, in general, from 0.01 or 0.1 to 0.5 or 1 percent by weight of the system, or more. Stated otherwise, the molar amount of acid is generally about 0.01 to 100 times the molar amount of aldehyde or acetal in the system. Preferably the system contains not more than 5 or 10 percent by weight water as noted above, and more preferably the system is non-aqueous.

The next step of the method involves (b) reacting the aldehyde or acetal with the pyrrole in the reaction system to form the dipyrromethane therein. The reaction temperature is not critical, but in general may be from −20 or 0 to 100° C., or more, and is preferably room temperature. The pressure of the system during the reaction is not critical, but is conveniently ambient pressure. The reaction may be carried out for any suitable time, typically up to 24 hours, and preferably up to one hour.

After the reaction step, the method involves (c) quenching the reaction system by adding a base thereto. The base is preferably added without simultaneously adding an organic solvent or water to the reaction system, and in a preferred embodiment the reaction system hence remains non-aqueous during quenching. In general, at least 1 equivalent of base per acid catalyst, up to 10 equivalents of base per acid catalyst, is added. The base may conveniently be added as a pure or neat substance (which may be a liquid or dry powder), a slurry in pyrrole, etc. The method then involves (d) separating the catalyst from the (preferably non-aqueous) reaction system, preferably by a filtration technique (such as suction filtration or pressure filtration) or a gravity technique (such as centrifugation or settling, e.g., with subsequent decanting); and then (e) separating the pyrrole from the (preferably non-aqueous) reaction system to produce the dipyrromethane as a residual (e.g., by pumping off or evaporating the pyrrole). As noted above, the method may optionally include the further step of (f) crystallizing the resultant dipyrromethane, which crystallization may be carried out in accordance with conventional techniques.

One embodiment of the present invention is a reaction schematically represented as follows:

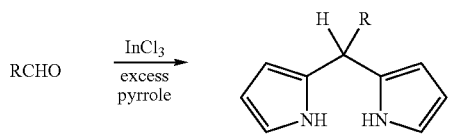

The present invention further provides a method of making a bis(dipyrrinato)metal complex. The method may be conveniently carried out in a single step (i.e., a "single pot" or "single flask" reaction). In general, the method comprises reacting a dipyrromethane produced as described herein with an oxidant and a metal salt to produce said bis(dipyrrinato)metal complex. Any suitable oxidant may be employed, including but not limited to of DDQ, o-chloranil, or p-chloranil. Any suitable metal salt can be used, including but not limited to zinc, palladium, copper, nickel, or cobalt salts (though in our hands some salts did not work as noted further below). Zinc salts are currently preferred. The salts may be formed with any suitable counterion(s), including but not limited to acetate, chloride, acac (acetylacetenate), etc. The reaction temperature is not critical, and may for example be from 0 to 100° C. Room temperature is currently preferred. The reacting step may be carried out in any suitable solvent, including but not limited to dichloromethane, tetrahydrofuran, toluene, chloroform, and mixtures thereof. In general, the solvent is a non-aqueous solvent.

The present invention further provides a method of disassembling a bis(dipyrrinato)metal complex such as produced above to produce separate dipyrrin groups. The method generally involves reacting a bis(dipyrrinato)metal complex with a thiol reagent, preferably under neutral conditions, to disassemble the bis(dipyrrinato)metal complex into separate dipyrrin groups. Any suitable thiol reagent can be used, examples including but not limited to dithiothreitol, 2-mercaptoethanol, butanethiol, and dithioerythritol. Any suitable metal may be employed as above, including but not limited to zinc, palladium, copper, nickel or cobalt. As previously noted, the dipyrrins and in turn the bis (dipyrrinato)metal complex may be unsubstituted or substituted, and in one embodiment the complex is substituted with from 1 to 4 porphyrinic macrocycles (thus, each of the separate dipyrrin groups produced in the process in turn being dipyrrin-substituted porphyrinic macrocycles which may be used as described below). The reaction temperature is not critical and may for example be from 0 to 100° C., with room temperature currently preferred. Any of a variety of solvents may be employed, examples including but not limited to chloroform, dichloromethane, tetrahydrofuran, toluene, and mixtures thereof.

The present invention further provides a method of synthesizing a dipyrrin-substituted porphyrinic macrocycle, which method generally involves (a) coupling a porphyrinic macrocycle and a bis(dipyrrinato)metal complex (such as produced by a method described above) to form a reaction product; and then (b) treating said reaction product with a thiol reagent to disassemble said reaction product and form said dipyrrin-substituted porphyrinic macrocycle. The coupling step may be carried out by any suitable means, such as by a Suzuki reaction or a Sonogashira reaction. For such reactions one of either the porphyrinic macrocycle and the bis(dipyrrinato)metal complex will be substituted with a first member of a reaction pair (e.g., a halogen such as fluoro, chloro, bronco, or iodo; a triflate) and the other of either the porphyrinic macrocycle and the bis(dipyrrinato)metal complex will be substituted with a corresponding second member of a reaction pair (e.g., dialkyl boronate, boronic acid or a derivative thereof, ethyne), with the members of the reaction pair selected to provide a covalent coupling between the two groups under the selected reaction conditions. Reaction conditions for Sonogashira or Suzuki couplings are well known and in general involve the presence of a palladium catalyst (non-limiting examples of which are Pd(Oac)$_2$, Pd$_2$(dba)$_3$, Pd(PPh$_3$)$_2$Cl$_2$, Pd(PPh$_3$)$_4$, etc.) and a base such as a triethylamine, diisopropylethylamine, KOH, K$_3$PO$_4$, K$_2$CO$_3$, Na$_2$CO$_3$, pyridine, Ba(OH)$_2$, etc. The second step (b) is a decoupling or disassembling step and is carried out as described above.

A still further aspect of the present invention is a method of synthesizing a dipyrrin-substituted porphyrinic macrocycle, comprising: condensing a dipyrromethane-dicarbinol with a dipyrrin-substituted dipyrromethane in a weakly polar solvent in the presence of a Lewis acid to produce a dipyrrin-substituted porphyrinic macrocycle. This reaction is generally carried out under conditions as described in commonly owned, copending application Ser. No. 09/962, 742 (published as US-2003-0096978-A1 on May 22, 2003). In general, the reaction is carried out in a solvent having a dielectric constant of about 20, 15, or 10 or less at room temperature (e.g., 25° C.), such as hydrocarbons, chlorinated hydrocarbons, ethers, esters, glymes, tributyl borate, carbon disulfide, and mixtures thereof. Any suitable electron pair acceptor may be used as the Lewis acid, examples including but not limited to CsCl, SmCl$_3$.6H$_2$O, InCl$_3$, CrF$_3$, AlF$_3$, Sc(OTf)$_3$, TiF$_4$, BEt$_3$, GeI$_4$, EuCl$_3$.nH$_2$O, LaCl$_3$, and Ln(OTf)$_3$ where Ln=lanthanide. The concentration thereof may range, for example, from 0.001 or 0.01 nmol/L to 100 or 500 mmol/L, or more. As above, the dipyrromethane-dicarbinol may have at least one porphyrinic macrocycle covalently coupled thereto, which porphyrinic macrocycle may be metalated, with the condensing step being carried out without demetalation of the porphyrinic macrocycle.

A further aspect of the present invention is a method of synthesizing a trans-(dipyrrin)$_2$-porphyrinic macrocycle, comprising: reacting a dipyrrin-carboxaldehde with a dipyrromethane in the presence of an acid catalyst to produce said trans-(dipyrrin)$_2$-porphyrinic macrocycle. Any suitable acid catalyst may be used, including but not limited to trifluoroacetic acid, $BF_3.O(Et)_2$ and $NH_4Cl$, trichloroacetic acid, etc.). The reacting step may be carried out at any suitable temperature, such as from 0 to 100° C. (preferably room temperature), and in any suitable solvent, examples including but not limited to dichloromethane, tetrahydrofuran, toluene, acetonitrile, chloroform, and mixtures thereof.

The methods and intermediates described herein may be used to produce a porphyrinic macrocycle having from 1 to 4 dipyrrin groups substituted thereon. As indicated above, the dipyrrins are preferably substituted on the porphyrinic macrocycle at the meso and/or beta positions of the porphyrinic macrocycle, and the dipyrrins are preferably coupled at or by the 1, 2, 3, 5, 7, 8 or 9 position of the dipyrrin. In one preferred embodiment, the porphyrinic macrocycle has two dipyrrins trans substituted thereon (and may optionally include additional dipyrrins substituted at additional locations thereon). The dipyrrin-substituted porphyrinic macrocycles of the present invention are useful, among other things, for the production of polymers thereof which may be immobilized or coupled to a substrate and used as light harvesting rods, light harvesting arrays, and solar cells, as described for example in U.S. Pat. No. 6,407,330 to Lindsey et al. or U.S. Pat. No. 6,420,648 to Lindsey. Dipyrrin-substituted porphyrinic macrocycles are also useful immobilized to a substrate for making charge storage molecules and information storage devices containing the same. Such charge storage molecules and information storage devices are known and described in, for example, U.S. Pat. No. 6,208,553 to Gyko et al.; U.S. Pat. No. 6,381,169 to Bocian et al.; and U.S. Pat. No. 6,324,091 to Gryko et al. The dipyrrin-substituted porphyrinic macrocycle may be comprise a member of a sandwich coordination compound in the information storage molecule, such as described in U.S. Pat. No. 6,212,093 to Li et al. or U.S. Pat. No. 6,451,942 to Li et al.

The present invention is explained in greater detail in the Examples set forth below.

EXAMPLES

A. Materials and Methods.

General. $^1$H NMR (400 MHz) spectra were recorded in $CDCl_3$ unless noted otherwise. $CH_2Cl_2$ (ACS grade), hexanes (ACS grade), ethyl acetate (ACS grade) and powdered NaOH (20–40 mesh beads) were used as received. The acids employed in this study were of the following grades (and were used in quantities without correction for less than 100% purity): trifluoroacetic acid (99%), trichloroacetic acid (98%), oxalic acid (97%), taurine (99%), malonic acid (99%), formic acid (98%), acetic acid (99.99%), $NH_4Cl$ (99.5%), $MgBr_2$ (98.5%), $Yb(OTf)_3$ (99.99%), $InCl_3$ (98%), Sc(OTf) (99%), and $CeCl_3$ (99.9%). All other chemicals including aldehydes were of reagent grade and were used as obtained. The earliest characterization data for dipyrromethanes prepared by one-flask syntheses are as follows: 1,[7] 5,[16] 6,[34] 7,[16,35] 8,[3] 9,[36] and 10.[11] Each compound prepared herein was characterized by GC, elemental analysis, mp, and $^1$H NMR spectroscopy.

Quality of Pyrrole. Pyrrole slowly discolors on standing. To determine how the purity of the dipyrromethane depends on the quality of the pyrrole employed, parallel reactions were performed using undistilled pyrrole or distilled pyrrole using a 100:1 ratio of pyrrole:benzaldehyde and $InCl_3$ at room temperature for 1 h. With undistilled pyrrole, the mixture was pale green; the GC yield was 89.8%; the yield upon recrystallization was 61% (97.3% purity by GC). With distilled pyrrole, the reaction mixture was pale yellow; the GC yield was 91.0%; the yield upon recrystallization was 68% (96.7% purity by GC). Given these differences, we employed distilled pyrrole throughout our experiments. Pyrrole (reagent grade) was distilled over calcium hydride before use.

Quantitative TLC. Unreacted benzaldehyde was examined by TLC analysis [silica, hexanes/ethyl acetate (4:1)] using known concentrations of benzaldehyde as standards, a method that enables quantitative analysis.[30] The standard samples corresponded to yields of 0.1%–50%. Each TLC plate was spotted with a reaction sample and at least two standards for visual comparison. In this manner, the yield of benzaldehyde could be bracketed. The lower limit of detection of unreacted benzaldehyde is 0.1%. We made no effort to assess quantities in the range of 50–100%; such amounts are designated as >50%. A typical example of TLC analysis [silica, hexanes/ethyl acetate (4:1)] for the synthesis of 5-phenyldipyrromethane with various acid catalysts was examined. Authentic samples were used for comparison. The trend in product distributions that was obtained from TLC analysis matches well with the results obtained upon GC analysis. Thus, when a Lewis acid such as $Yb(OTf)_3$ or $Sc(OTf)_3$ was used, the intensity of the spot corresponding to N-confused dipyrromethane was quite strong while that of tripyrrane was weak. On the other hand, when a Brønsted acid such as oxalic acid, trichloroacetic acid, or malonic acid was used, the intensity of the spot corresponding to N-confused dipyrromethane was weak while that of tripyrrane was strong. While this general trend is apparent, the close chromatography of the various species and the lack of sensitivity to other components limit the utility of TLC for gauging the purity of the dipyrromethane.

Gas Chromatography. Gas chromatography was carried out using an HP 6890 Series gas chromatograph equipped with an FID detector and a fused silica capillary column HP-5 (30 m×0.32 mm×2.5 μm). All samples were examined under the following temperature gradient: temp 1, 35° C. (5 min); temp 2, 315° C. (12 min); rate 20° C./min, total running 31 min. Relative yields were determined by direct integration of the peak areas of the gas chromatogram rather than by constructing calibration curves using standard solutions of each component. We demonstrated earlier that the detector had an approximately linear response to the amount of each component present.[16] GC-MS data were acquired using an HP 5890 GCD Series gas chromatograph using the same temperature gradient as described for GC analysis.

Variation in the workup process has little impact on the product distribution. Workup of the $InCl_3$ catalyzed condensation (100:1 ratio of pyrrole:benzaldehyde at room temperature for 1 h) by quenching with TEA or NaOH, or using ethyl acetate or $CH_2Cl_2$ as the GC injection solvent, gave nearly identical product distribution profiles. The only differences were in the appearance of several minor peaks in the 19–24 min region.

A control experiment where a sample of pyrrole and benzaldehyde (100:1) was injected into the GC instrument resulted in broad, low intensity peaks (9–11 min) as well as a peak due to 5-phenyldipyrromethane (at ~1% level). The latter is not due to carryover from the prior sample. We have previously shown that benzaldehyde and pyrrole react, albeit slowly and in low yield, upon heating in the absence of an acid to give the dipyrromethane.[16] Thus, samples from reaction mixtures where no reaction occurs can still give small amounts of the dipyrromethane as a GC artefact.

GC-MS data were obtained with high loading of samples in order to detect trace components. Assignment of peaks was done with comparison of background to avoid artifacts owing to bleeding of earlier eluting species (particularly isomers) that were present in very high amounts such as the dipyrromethane and tripyrrane.

Survey of acid catalysts. Analytical scale reactions of benzaldehyde (1.50 mmol) and pyrrole (150 mmol) in the presence of each catalyst (0.15 mmol) were performed at room temperature. Reactions were quenched after 1 h. Quantitative TLC analysis was performed as described above. GC analysis was done by removing 200-μL aliquots of the reaction mixture after quenching and then diluting with 800 μL of $CH_2Cl_2$.

Effect of pyrrole:benzaldehyde ratio and concentration of acids. Studies on the effect of the pyrrole:benzaldehyde ratio and the amount of added acid (TFA or $InCl_3$) on the product distribution were performed as illustrated for the following typical example (pyrrole:benzaldehyde 100:1): A mixture of pyrrole (26.8 g, 400 mmol) and benzaldehyde (424 mg, 4.00 mmol) was treated with 0.1 equiv of $InCl_3$. After 1, 2, 3, and 24 h, 250-μL aliquots from the reaction mixture were removed and immediately quenched by injection into a 500-μL solution of ethyl acetate/TEA (25:1), then filtered (in the case of $InCl_3$). These samples were examined by GC analysis as described above.

General Procedure Illustrated for 5-Phenyldipyrromethane (1).

A. Crystallization method. Pyrrole (347 mL, 5.00 mol) and benzaldehyde (5.35 g, 50.0 mmol) were added to a 500 mL single-neck round-bottomed flask containing a magnetic stir bar. The solution was degassed with a stream of argon for 10 min. $InCl_3$ (1.11 g, 5.00 mmol) was added and the mixture was stirred under argon at room temperature for 1.5 h. The mixture turned yellow during the course of the reaction. NaOH (6.0 g, 0.15 mol, 20–40 mesh beads) was added to quench the reaction.[i] Stirring for 45 min afforded a pale yellow mixture. The mixture was filtered (Fisher brand qualitative filter paper) using a Buchner funnel. The contents of the flask and the filtered material were washed with a small amount of pyrrole. The filtrate was concentrated using a rotary evaporator under vacuum (0.2 mm Hg); the evaporation flask was warmed at 40–50° C. and the collection trap was cooled with a dry ice-acetone bath. The collected pyrrole was set aside. The crude viscous residue in the evaporation flask was entrained with hexanes (3×50 mL) to remove traces of pyrrole.[ii] The resulting yellow solid was dissolved in 60 mL of ethanol/water (4:1)[iii] with heating by a water bath. The resulting yellow solution containing a very small amount of white powder was filtered (Fisher brand qualitative filter paper) and the filtrate was set aside overnight at room temperature, affording a first crop of pale yellow crystals [7.22 g, 65% yield; mp 99–100° C. (lit.[7] mp 102–103° C.); 96.7% purity by GC; Anal. Calcd for $C_{15}H_{14}N_2$: C, 81.05; H, 6.35; N, 12.60. Found: C, 81.04; H, 6.41; N, 12.67]. Concentration of the mother liquor afforded a second crop of pale brown crystals (1.22 g, 11% yield; 86.3% purity by GC). The second crop of crystals was recrystallized [18 mL of ethanol/water (4:1)] affording yellow crystals (1.05 g, 10% yield; 92.0% purity by GC) followed by another crystallization [16 mL, isopropanol/water (15:1)], affording pale yellow crystals (0.66 g, 6% yield; mp 99–100° C.; 96.8% purity by GC; Anal. Calcd for $C_{15}H_{14}N_2$: C, 81.05; H, 6.35; N, 12.60. Found: C, 80.90; H, 6.36; N, 12.57). The crops were combined, affording pale yellow crystals (7.88 g, 71% yield; calcd 96.7% purity by GC).

Notes: (i) It is essential to quench the reaction with a strong base (e.g., NaOH) and to stir the reaction mixture for a period thereafter (45 min). When the reaction mixture was quenched with an organic base (e.g., TEA) or not quenched at all, much of the indium material was still obtained upon filtration but the crude dipyrromethane was obtained as a blue material. The blue material proved very difficult to remove from the dipyrromethane by crystallization or charcoal, but could be removed by flash chromatography.

(ii) It is essential that the crude dipyrromethane be obtained as a solid largely free of pyrrole prior to initiating crystallization.

(iii) Attempts to crystallize the crude product in other solvents [e.g., $CH_2Cl_2$/hexanes, ethyl acetate/hexanes, ether/hexanes, THF/water] were not successful.

B. Column chromatography method: Pyrrole (139 mL, 2.00 mol) and benzaldehyde (2.13 g, 20.1 mmol) were condensed in the presence of 0.1 equiv of $InCl_3$ in a similar manner as described above. The crude product obtained after removal of pyrrole was purified by column chromatography [silica, 6 cm dia. ×14 cm, hexanes/$CH_2Cl_2$/ethyl acetate (7:2:1)]. The crude mixture was dissolved in $CH_2Cl_2$, then silica gel was added and the mixture was evaporated to dryness. The resulting powder was loaded on the top of the column. Elution (400–1400 mL of eluant) followed by concentration of the eluted product gave a white solid (3.64 g, 82% yield; mp 100° C.; >99% purity by GC; Anal. Calcd for $C_{15}H_{14}N_2$: C, 81.05; H, 6.35; N, 12.60. Found: C, 80.94; H, 6.39; N, 12.55). Note that chromatographic purification of the crude product using common solvents such as $CH_2Cl_2$ and/or hexanes/$CH_2Cl_2$ (1:1) was unsuccessful. Even careful chromatography on silica with hexanes/ethyl acetate (4:1) gave mixtures of the three components though this solvent system happened to be a good solvent for TLC analysis.

Applications.

5-(4-Methoxyphenyl)dipyrromethane (5). (A). The reaction of p-anisaldehyde (6.81 g, 50.0 mmol) with crystallization [ethanol/water (4:1)] afforded two crops of crystals: (crop 1) light brown crystals [5.17 g, 41% yield; nip 95–96° C. (lit.[16] mp 99° C.); 93.7% purity by GC; Anal. Calcd for $C_{16}H_{16}N_2O$: C, 76.16; H, 6.39; N, 11.10. Found: C, 75.75; H, 6.40; N, 10.98]; (crop 2) brown crystals (2.82 g, 23% yield; 91.0% purity by GC). Combination and recrystallization afforded light brown crystals (5.42 g, 43% yield; mp 98–99° C.; 97% purity by GC; Anal. Calcd for $C_{16}H_{16}N_2O$: C, 76.16; H, 6.39; N, 11.10. Found: C, 76.03; H, 6.36; N, 11.08).

(B). Reaction at the 20.0-mmol scale with chromatography [silica, hexanes/$CH_2Cl_2$/ethyl acetate (16:3:1)] afforded a yellow solid (3.12 g, 62% yield; mp 99° C.; >99% purity by GC; Anal. Calcd for $C_{16}H_{16}N_2O$: C, 76.16; H, 6.39; N, 11.10. Found: C, 76.06; H, 6.43; N, 10.99).

5-(4-Carbomethoxyphenyl)dipyrromethane (6). (A). The reaction of methyl 4-formylbenzoate (8.21 g, 50.0 mmol)

with crystallization [methanol/water (10:1)] afforded two crops of crystals: (crop 1) pale yellow crystals [7.84 g, 56% yield; mp 162–163° C. (lit.[34] mp 158° C.); 97.2% purity by GC; Anal. Calcd for $C_{17}H_{16}N_2O_2$: C, 72.84; H, 5.75; N, 9.9. Found: C, 72.59; H, 5.75; N, 9.79]; (crop 2) pale yellow crystals (2.66 g, 19% yield; mp 161–162° C.; 96.5% purity by GC; Anal. Calcd for $C_{17}H_{16}N_2O_2$: C, 72.84; H, 5.75; N, 9.99. Found: C, 72.34; H, 5.83; N, 9.90). Altogether, 10.5 g (75% yield; calcd 97.0% purity by GC) was obtained.

(B). Reaction at the 20.0-mmol scale with chromatography [silica, hexanes/$CH_2Cl_2$/ethyl acetate (7:2:1)] afforded a white solid (4.20 g, 75% yield; mp 159–160° C.; >99% purity by GC; Anal. Calcd for $C_{17}H_{16}N_2O_2$: C, 72.84; H, 5.75; N, 9.99. Found: C, 72.48; H, 5.68; N, 9.74).

5-(Pentafluorophenyl)dipyrromethane (7). (A). The reaction of pentafluorobenzaldehyde (9.80 g, 50.0 mmol) with crystallization [ethanol/water (4:1)] afforded two crops of crystals: (crop 1) pale white crystals [8.27 g, 53% yield; mp 130–131° C. (lit.[16] mp 131–132° C.); >99% purity by GC; Anal. Calcd for $C_{15}H_9F_5N_2$: C, 57.70; H, 2.91; N, 8.97. Found: C, 57.92; H, 2.76; N, 9.04]; (crop 2) pale white crystals (4.05 g, 26% yield; mp 129–130° C.; >99% purity by GC; Anal. Calcd for $C_{15}H_9F_5N_2$: C, 57.70; H, 2.91; N, 8.97. Found: C, 57.66; H, 2.82; N, 8.84). Altogether, 12.3 g (79% yield; calcd >99% purity by GC) was obtained.

(B). Reaction at the 20.0-mmol scale with chromatography twice [silica, hexanes/$CH_2Cl_2$/ethyl acetate (10:2:1)] afforded a white solid (5.00 g, 80% yield; mp 131° C.; 98.0% GC purity; Anal. Calcd for $C_{15}H_9F_5N_2$: C, 57.70; H, 2.91; N, 8.97. Found: C, 57.64; H, 3.02; N, 8.95).

5-(Pentyl)dipyrromethane (8). The reaction of hexanal (5.01 g, 50.0 mmol) was performed in the standard way. The viscous liquid obtained upon removal of pyrrole was chromatographed twice [silica, hexanes/$CH_2Cl_2$/ethyl acetate (16:3:1); hexanes/ethyl acetate (9:1.)], affording a yellow oil (6.70 g, 62% yield; 94.3% purity by GC; Anal. Calcd for $C_{14}H_{20}N_2$: C, 77.73; H, 9.32; N, 12.95. Found: C, 77.63; H, 9.48; N, 12.71).

Dipyrromethane (9). (A). A mixture of paraformaldehyde (1.50 g, 50.0 mmol) and pyrrole (347 mL, 5.00 mol) in a 500-mL flask was degassed with a stream of argon for 10 min at room temperature. The mixture was heated at 55° C. for about 10 min under argon to obtain a clear solution. $InCl_3$ (1.11 g, 5.00 mmol) was then added and the mixture was stirred at 55° C. for 2.5 h. The heat source was removed and NaOH (6.0 g. 0.15 mol) was added. The mixture was stirred for 1 h, then filtered. The crude solid obtained after removing pyrrole was extracted with 20% ethyl acetate/hexanes mixture (5×50 mL). The solvent was evaporated. Crystallization [methanol/water (4:1)] afforded pale white crystals [3.29 g, 45% yield; mp 70–71° C. (lit.[36] mp 74° C.); 94.6% purity by GC; Anal. Calcd for $C_9H_{10}N_2$: C, 73.94; H, 6.89; N, 19.16. Found: C, 74.00; H, 6.81; N, 19.15].

(B). The same procedure at the 20.0-mmol scale with chromatography [silica, hexanes/$CH_2Cl_2$/ethyl acetate (7:2:1)] afforded a white solid (1.84 g, 63% yield; mp 75° C.; >99% purity by GC; Anal. Calcd for $C_9H_{10}N_2$: C, 73.94; H, 6.89; N, 19.16. Found: C, 74.18; H, 6.92; N, 19.14).

5-Mesityldipyrromethane (10). (A). A mixture of mesitaldehyde (7.42 g, 50.0 mmol) and pyrrole (347 mL, 5.00 mol) in a 500-mL single-neck round-bottomed flask was degassed with a stream of argon for 10 min. $MgBr_2$ (4.60 g, 25.0 mmol) was added and the mixture was stirred for 1.5 h at room temperature. The tan mixture was treated with powdered NaOH (10.0 g, 0.25 mol). The mixture was stirred for 1 h, then filtered. The crude solid obtained upon removal of pyrrole was extracted with 20% ethyl acetate/hexanes (7×100 mL) and the extract was gravity filtered through a pad of silica (80 g). The eluted solution was concentrated to obtain a yellow solid. Crystallization [ethanol/water (4:1)] afforded pale yellow crystals [7.00 g, 53% yield; 93% purity by GC; nip 166–167° C. (lit.[11] mp 166–167° C.); Anal. Calcd for $C_{18}H_{20}N_2$: C, 81.78; H, 7.63; N, 10.60. Found: C, 81.16; H, 7.67; N, 10.19].

(B). The same procedure was performed at the 20.0-mmol scale. Following silica-pad filtration, chromatography [silica, toluene/$CH_2Cl_2$ (1:1)] afforded a yellow solid (3.43 g, 65% yield; mp 165–166° C.; 92.7% purity by GC; Anal. Calcd for $C_{18}H_{20}N_2$: C, 81.78; H, 7.63; N, 10.60. Found: C, 81.89; H, 7.66; N, 10.36).

Large-Scale Synthesis of 5-Phenyldipyrromethane (1).

Pyrrole (5.20 L, 75.0 mol; recycled) and benzaldehyde (79.8 g, 0.752 mol) were added to a 12-L two-neck round-bottomed flask equipped with a mechanical stirrer. The solution was degassed with a stream of argon for 1 h. $InCl_3$ (16.7 g, 75.5 mmol) was added and the mixture was stirred under argon at room temperature for 1.5 h. The color of the solution was yellow during the course of the reaction. The reaction was quenched by the addition of NaOH (90.1 g, 2.25 mol; 20–40 mesh beads). The mixture was stirred for 1 h. The stirrer was stopped and the mixture was allowed to settle for 1 h. The mixture was filtered (Fisher brand qualitative filter paper) using a Buchner funnel. The flask and filtered material on the funnel was washed with pyrrole (350 mL). The filtered material after drying under vacuum with warming for 4 h constituted 118 g. The filtrate was concentrated using a rotary evaporator under vacuum (0.2 mill Hg) at 40–60° C. and the trap was cooled in a dry ice-acetone bath, affording 5.30 L of recovered liquid and a crude viscous residue in the evaporation flask. The crude viscous residue was entrained with hexanes (4×450 mL) to remove traces of pyrrole, affording a pale yellow solid (87.0% GC purity; containing 7.9% of N-confused dipyrromethane 2 and 1.0% of tripyrrane 3). Recrystallization [ethanol/water (4:1), 1 L] afforded a first crop of pale yellow crystals [98.9 g; mp 100–101° C. (lit.[7] mp 102–103° C.); 94.8% purity by GC; Anal. Calcd for $C_{15}H_{14}N_2$: C, 81.05; H, 6.35; N, 12.60. Found: C, 80.84; H, 6.40; N, 12.62]. Concentration of the mother liquor afforded a second crop of yellow crystals (6.00 g; mp 98–99° C.; 92.3% purity by GC; Anal. Calcd for $C_{15}H_{14}N_2$: C, 81.05; H, 6.35; N, 12.60. Found: C, 80.84; H, 6.37; N, 12.57). The mother liquor was concentrated affording a third crop (14.1 g; 88.7% purity by GC) and a fourth crop (3.33 g; 83.1% purity by GC) of crystals. Crops three and four were combined and recrystallized [ethanol/water (4:1)] affording pale brown crystals (10.6 g; mp 99–100° C.; 94.0% purity by GC; Anal. Calcd for $C_{15}H_{14}N_2$: C, 81.05; H, 6.35; N, 12.60. Found: C, 80.88; H, 6.39; N, 12.63). Altogether, 116 g of the title compound was obtained (70% yield; calcd 94.2% purity by GC).

The filtered material (118 g) from the crude reaction mixture exceeds the mass of the $InCl_3$ (16.7 g) and NaOH (90.1 g); the difference is attributed to water of hydration (maximally ca. 13.5 g originating from the condensation). The recovered liquid (5.30 L), which contains predominantly pyrrole and residual water, was distilled. The recovered pyrrole (4.92 L, 90% recovery based on unreacted pyrrole) was suitable for reuse.

B. Results and Discussion

I. Analytical Methods. We first examined the applicability of various analytical techniques (TLC, NMR spectroscopy, GC, and elemental analysis) for identifying and quantifying the products of the pyrrole-aldehyde condensation. The model reaction of pyrrole+benzaldehyde was selected for these studies. The dominant products formed in this reaction are 5-phenyldipyrromethane (1), N-confused 5-phenyldipyrromethane (2) and 5,10-diphenyltripyrrane (3) (Scheme 1). We have used pure authentic samples of 1,[16] 2,[16] and 3[29] for direct comparison during the analysis. The following results were obtained upon reaction of a 100:1 ratio of pyrrole:benzaldehyde at room temperature with catalysis by $InCl_3$ (identical results were obtained with TFA catalysis).

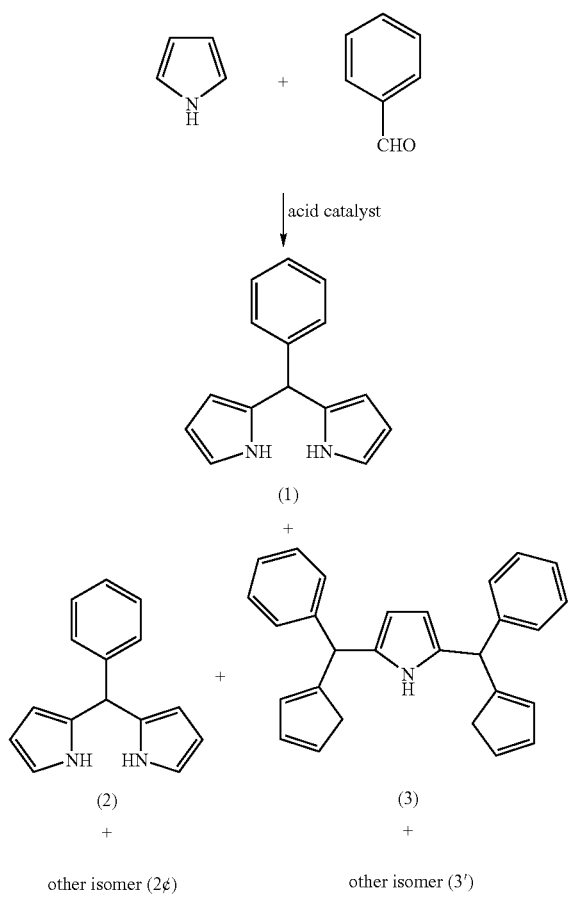

(a) TLC Analysis. Compounds 1, 2 and 3 closely chromatograph on silica [hexanes/ethyl acetate (4/1)] giving $R_f$ values as follows: 1, 0.53; 3, 0.48; 2, 0.38. The order of elution changed on alumina in the same solvent system: 1, 0.52; 2, 0.39; 3, 0.32. Quite careful chromatography is required to distinguish 1, 2 and 3. Benzaldehyde is readily distinguished on silica, however ($R_f$=0.64). TLC can be used to quantitate the amount of unreacted benzaldehyde through the use of a series of standards of known concentration.[30] The limit of detection corresponds to 0.1% unreacted benzaldehyde for a reaction of 100:1 pyrrole:benzaldehyde.

(b) Elemental Analysis. The synthesis of dipyrromethanes is such that a satisfactory elemental analysis (<0.4% deviation from calculated composition) for an isolated dipyrromethane may not necessarily imply the desired level of purity. Elemental analysis is obviously blind to the presence of an N-confused dipyrromethane, which is a dipyrromethane isomer. Perhaps less obvious is the lack of sensitivity to the presence of contamination by a tripyrrane. A tripyrrane is an oligomer of the dipyrromethane and has an elemental ratio similar to that of the dipyrromethane. For example, in the case of 5-phenyldipyrromethane (1) ($C_{1.000}H_{0.933}N_{0.133}$), 5,10-diphenyltripyrrane (3) ($C_{1.000}H_{0.885}N_{0.115}$) can be present as a contaminant at a level of up to 15.5% yet the mixture will still fall within the 0.4% error limit upon elemental analysis. For 5-mesityldipyrromethane (10), the 5,10-dimesityltripyrrane contaminant can reach 17%, and for dipyrromethane itself (9) (no meso substituent), tripyrrane can reach up to 46% without exceeding the accepted error limits. Thus, an isolated dipyrromethane may give a satisfactory elemental analysis despite the presence of substantial amounts of N-confused dipyrromethane and tripyrrane contaminants.

(c) NMR Spectroscopy. The $^1H$ NMR spectra of 1, 2, 3 are shown in FIG. 1. Each peak was assigned by 2D-NMR (HH-COSY and NOESY) measurements. The spectrum of a crude reaction mixture (following neutralization and removal of pyrrole) is also shown. While 1 is the dominant species, the presence of 2 and 3 can be readily detected by the presence of characteristic (and non-overlapping) peaks of the 5-phenyldipyrromethane meso-$H^5$ (~5.4 ppm), N-confused 5-phenyldipyrromethane $H^7$ (flanking the β-substituent, ~6.5 ppm), and the 5,10-diphenyltripyrrane $H^7$ (2 protons at the β-positions of the central pyrrole ring, ~5.7 ppm). The relative amounts of the three species in the crude reaction mixture can be calculated by integration of these characteristic peaks, taking into account the 1:1:2 ratio of the number of hydrogens: 1/2/3=88:9:3. This method is satisfactory for identifying the presence of the N-confused 5-phenyldipyrromethane and 5,10-diphenyltripyrrane at the few percent level or greater.

Figure 2:
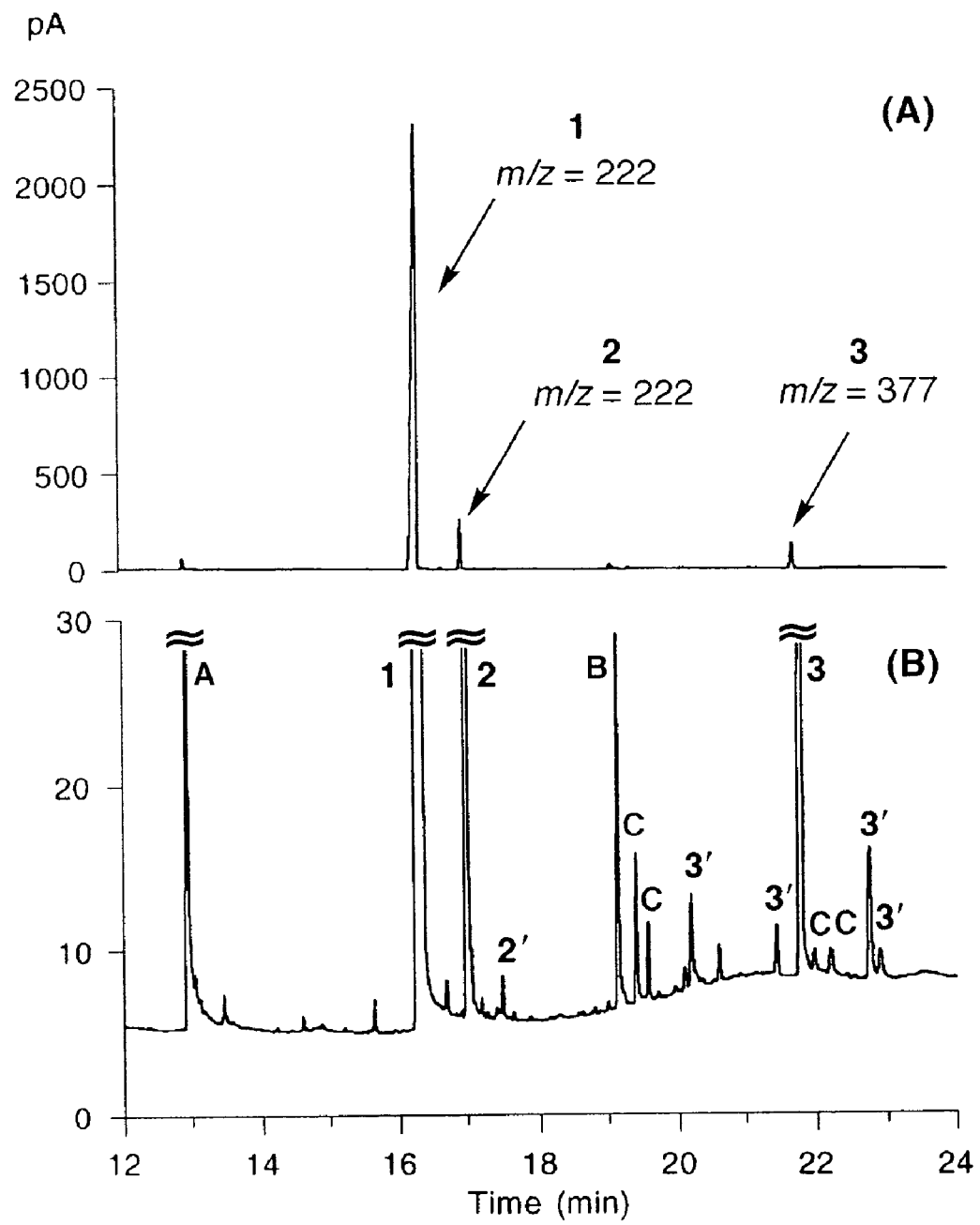
FIG. 2. Typical GC trace of the crude mixture obtained from the condensation of pyrrole and benzaldehyde (100:1, 0.1 equiv of $InCl_3$, 3 h) using a GC (FID) with temperature gradient (temp 1, 35° C. (5 min); temp 2, 315° C. (12 min); rate 20° C./min, total running 31 min). The peaks were confirmed with standard samples of 1, 2, and 3 or assigned in separate runs by GC-MS analysis. The peaks labeled as 2' and 3' are isomers of N-confused 5-phenyldipyrromethane (2) and 5,10-diphenyltripyrrane (3), respectively. The trace in (B) is an expansion of the trace in (A).

(d) Gas Chromatography. We previously reported that the GC trace of the crude reaction mixture, obtained with TFA catalysis, shows three major peaks.[16] The GC trace of the crude reaction mixture obtained with 0.1 equiv of $InCl_3$ and a pyrrole:benzaldehyde ratio of 100:1 for 1 h also shows three major peaks (FIG. 2A) that are assigned as 1 ($t_R$=16.4 min), 2 ($t_R$=17.0 min) and 3 ($t_R$=21.8 min) based on comparison with authentic samples. Closer scrutiny of the same GC trace upon amplification of the scale reveals a number of additional minor peaks (FIG. 2B). The appearance and intensity of these minor peaks depend on the reaction conditions (catalyst, reaction time, and pyrrole:benzaldehyde ratio). For example, some of the minor peaks seen in $InCl_3$ catalyzed reactions are not observed in TFA catalyzed reactions.

Figure 3:
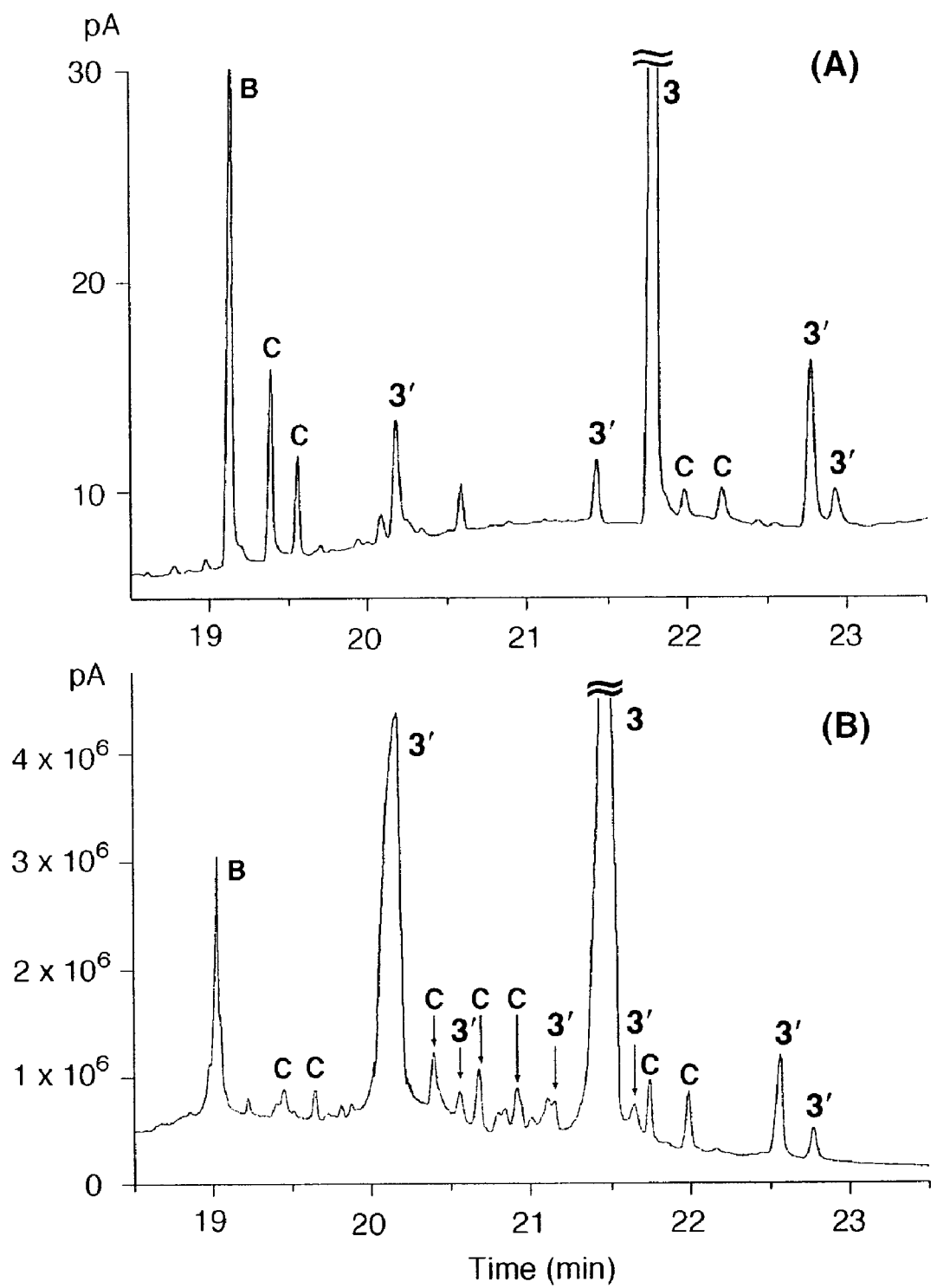
FIG. 3. Expanded region of the GC traces of the crude mixture from the condensation of pyrrole and benzaldehyde (100:1, 0.1 equiv of $InCl_3$, 3 h). (A) Further expansion of the traces in FIG. 2 (using FID). (B) The same reaction sample upon analysis by GC-MS with the same temperature gradient and a nearly identical column. Numerous peaks from $t_R$=20.5 to 21.5 min are attributed to tripyrrane isomers (3', m/z=377) and unknown species "C" (m/z=310, consistent with a benzyl dipyrrin).
Figure 4:
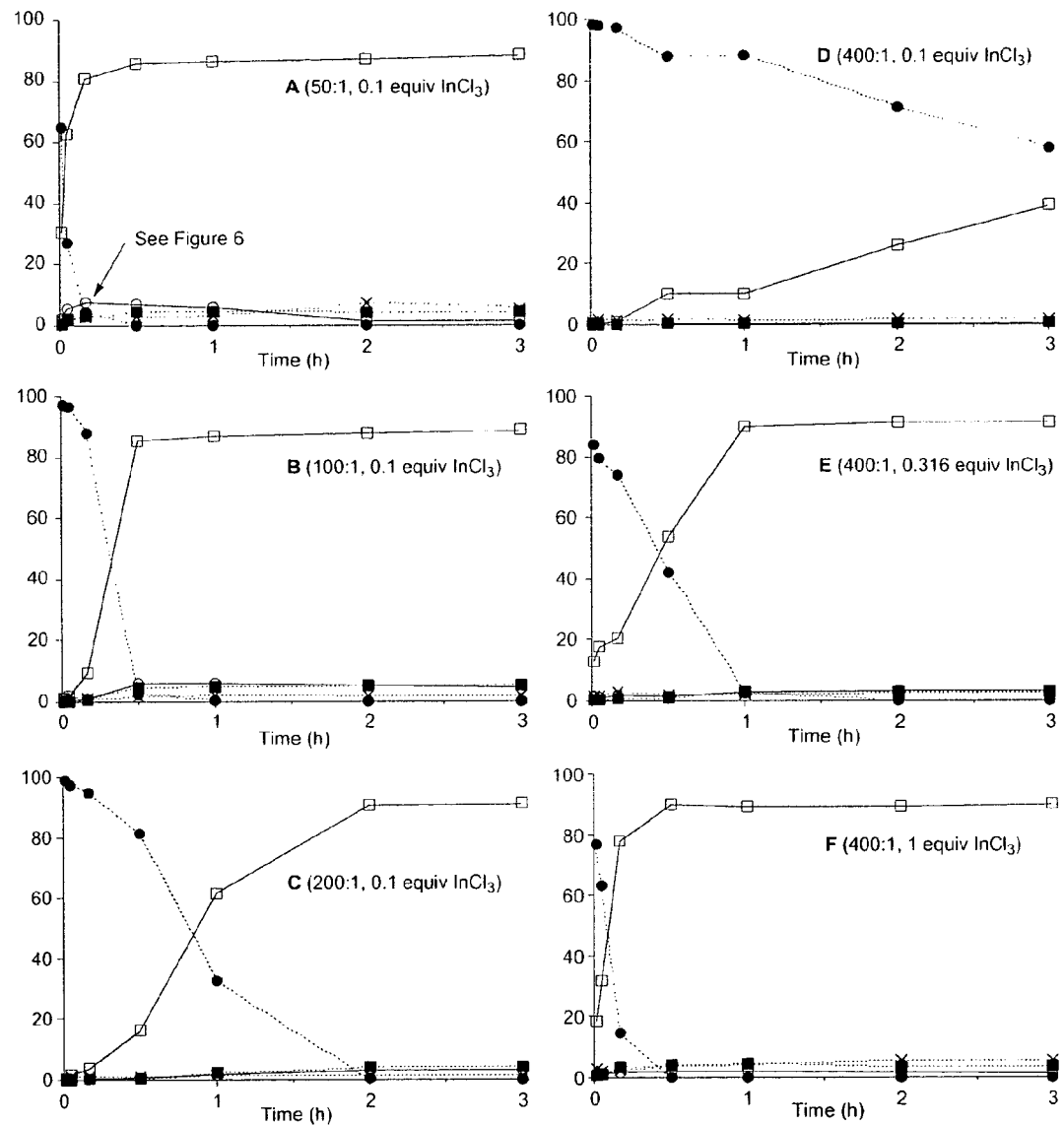
FIG. 4. Effect of pyrrole:benzaldehyde ratio on the reaction rate and product distribution. The data were obtained by GC analysis. The pyrrole:benzaldehyde ratios and the amount of $InCl_3$ are specified in panels A–F. The early timepoints were at 1, 3, and 10 mil. Legend: 5-phenyldipyrromethane (1, □); N-confused 5-phenyldipyrromethane (2, ■); 5,10-diphenyltripyrrane (3, ○); benzaldehyde ( ); and the sum of all other volatile components (X).

The region between 17 and 24 min was further expanded as shown in FIG. 3. Some differences in the chromatogram are observed based on the choice of detector (FID or EC). We employed GC-MS to gain information concerning the identity of the various minor peaks. The peaks in the chromatograms of FIGS. 2 and 3 can be assigned as follows.

(i) The peak at $t_R$=8.2 min stems from unreacted benzaldehyde, which was observed at early times but not after 1 h of reaction (not shown).

(ii) Broad, low-intensity peaks around 9–11 min were observed in some monitoring experiments (including a blank sample of benzaldehyde and pyrrole alone) when both pyrrole and benzaldehyde were present. Such peaks are assumed to derive from reaction of benzaldehyde and pyrrole upon GC analysis; i.e., they are GC artifacts.

(iii) The peak at 12.9 min (denoted "A") shows m/z=157 by GC-MS, which is consistent with a benzyl pyrrole ($C_{11}H_{11}N$) structure.

(iv) The peaks due to 1 ($t_R$=16.4 min), 2 ($t_R$=17.0 mil) and 3 ($t_R$=21.8 min) were readily assigned based on the use of authentic standards.

(v) GC-MS analysis showed the peak at 17.6 min to have m/z=222, the same as 2, implying this peak stems from an isomer of 2. We label this peak 2'.
(vi) The peak at 18.8 min (denoted "B") has m/z=413, which is attributed to a chloro-substituted tripyrrane of unknown structure. Peak B virtually disappeared when the reaction was performed in TFA, suggesting InCl$_3$ as the source of the chloride.
(vii) Most of the remaining peaks fall into two categories depending on the observed m/z. Four of the peaks have m/z=377, the same as 3, and are labeled 3' indicating they are isomers of 3.
(viii) A number of other peaks have m/z=310, consistent with a benzyldipyrrin (e.g., 4, Chart 2) isomer or tautomer (C$_{22}$H$_{18}$N$_2$), and are labeled "C".

Chart 2

4

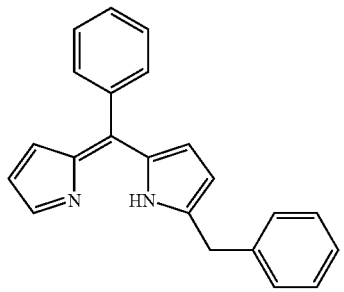

The apparent presence of additional isomers of the dipyrromethane and tripyrrane was at first surprising. However, there are three 5-phenyldipyrromethanes given the possibility of α or β substitution. Thus, 1 is the αα isomer, 2 is the αβ isomer, and 2' likely stems from the ββ isomer. There are 10 possible regioisomers of a 5,10-diphenyltripyrrane (3 and 3') depending on whether the four substitutions occur at the α- or β-positions. Moreover, the two meso-carbons in the tripyrrane are both chiral, leading to stereoisomers in all tripyrranes lacking a central plane of symmetry. The regioisomers are shown in Chart 3.

Chart 3

4α isomer (the parent tripyrrane):

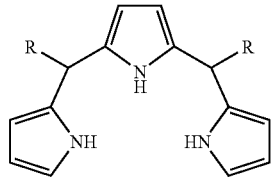

3α1β isomers:

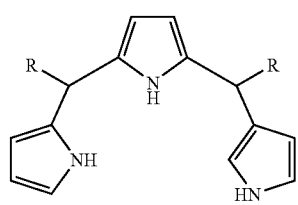

-continued

2α2β isomers:

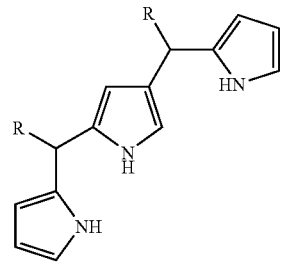

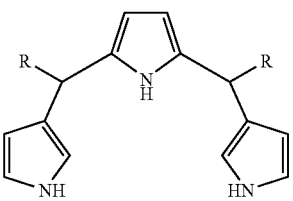

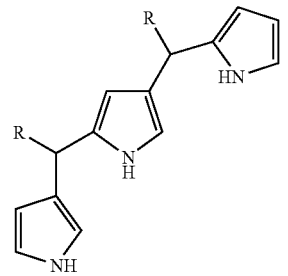

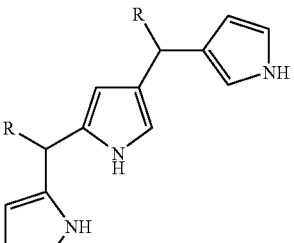

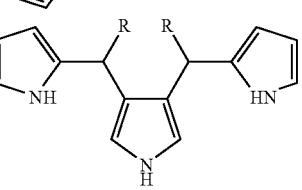

3β1α isomers:

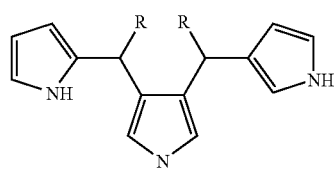

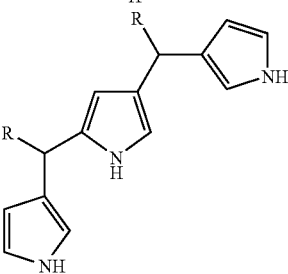

4β isomer:

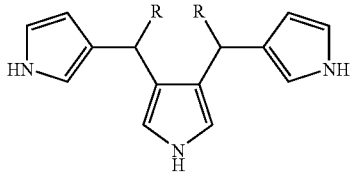

In the GC trace (FIG. 3A), four peaks are attributed to 3' isomers, while in the GC-MS trace (FIG. 3B), seven peaks with m/z=377 are assigned as 3' isomers. The structures of the components that give rise to peaks "C" are not known, but eight benzyldipyrrin isomers with various α/β substitution patterns are possible (and additional azafulvene tautomers are conceivable). It is noteworthy that a benzyldipyrrin analogous to 4 has been isolated as a side product in a porphyrin-forming reaction.[31] A mechanism for the formation of 4 in pyrrole-aldehyde condensations has been proposed.[32]

In the following studies, the relative yields of 1, 2, and 3 have been identified by GC analysis. The remaining peaks (except benzaldehyde and any known GC artifacts) in the 12–31 min region have been grouped as "other volatile components". While the magnitude of the latter species are typically in the 1–5% range, these are the components that must be removed during purification and which are not easily identified by $^1$H NMR spectroscopy or elemental analysis. We have employed GC in conjunction with other analytical methods in the following survey to identify improved reaction conditions and workup procedures.

II. Survey of Acids

A. Effects of Acid. A series of acids was examined in the one-flask synthesis of 5-phenyldipyrromethane. The acids include eight Brønsted acids with a range of $pK_a$ values from 0.3 (TFA) to 9.3 (NH$_4$Cl), and five Lewis acids [Yb(OTf)$_3$, InCl$_3$, Sc(OTf)$_3$, MgBr$_2$ and CeCl$_3$] that span a range of hard/soft acids. Each condensation was performed with a 50:1 or 100:1 ratio of pyrrole:benzaldehyde at room temperature for 30 min or 1 h. Samples were analyzed by TLC to quantitate the amount of unreacted benzaldehyde; by GC to assess the relative amount of 1, 2, 3, and other species; and visually to gauge the amount of discoloration of the reaction medium. The ideal acid would give negligible unreacted benzaldehyde, a high yield of 1, and no discoloration of the reaction medium. While hard to quantify, the discoloration of the reaction medium signals formation of materials that diminish the yield and complicate the purification.

The acids examined and the observations for the 100:1 reaction are listed in Table 1. Similar results were obtained with the 50:1 pyrrole:benzaldehyde reaction. Several Brønsted acids (TFA, trichloroacetic acid, oxalic acid, and malonic acid) readily formed the dipyrromethane (>80% by GC) with near complete consumption of benzaldehyde. Weaker Brønsted acids showed lower reactivity as a catalyst. Brønsted acids that gave good yields of dipyrromethanes generally also gave a substantial amount (>10%) of tripyrrane 3, negligible (<1.5%) N-confused dipyrromethane 2, and discolored reaction mixtures. The direct crystallization of the dipyrromethane from discolored reaction mixtures was typically quite problematic.

TABLE 1

Effects of different acids on the pyrrole-benzaldehyde condensation.[a]

| Acid ($pK_a$) | Solubility[b] | Color[c] | Unreacted benzaldehyde[d] | Relative Amounts (%) by GC[e] | | | |
|---|---|---|---|---|---|---|---|
| | | | | 1 | 2 | 3 | Other[f] |
| Brønsted acids | | | | | | | |
| Trifluoroacetic (0.3) | soluble | ++++ | 0.1%–0.5% | 84.7 | 1.5 | 12.1 | 1.7 |
| Trichloroacetic (0.70) | soluble | +++ | 0.1%–0.5% | 86.6 | 1.5 | 9.9 | 2.0 |
| Oxalic (1.2) | partially | +++ | 0.1%–0.5% | 84.1 | 1.4 | 11.6 | 2.9 |
| Taurine (1.5) | insoluble | − | >50% | <1 | n.o.[g] | n.o. | 2.8 |
| Malonic (2.8) | partially | +++ | 0.1%–0.5% | 80.4 | 1.2 | 14.8 | 2.6 |
| Formic (3.8) | soluble | + | >50% | 13.1 | n.o. | 2.0 | 3.3 |
| Acetic (4.8) | soluble | − | >50% | <2 | n.o. | n.o. | n.o. |
| NH$_4$Cl (9.3) | insoluble | − | >50% | <1 | n.o. | n.o. | n.o. |
| Lewis acids | | | | | | | |
| Yb(OTf)$_3$ | partially | + | 0.1%–0.5% | 75.4 | 20.1 | 1.1 | 3.4 |
| InCl$_3$ | insoluble | + | 0.1%–0.5% | 88.0 | 7.5 | 3.1 | 1.4 |
| Sc(Otf)$_3$ | insoluble | ++ | 0.1%–0.5% | 71.2 | 23.2 | 1.3 | 4.3 |
| MgBr$_2$ | insoluble | + | 0.5%–1% | 82.7 | 4.0 | 5.4 | 1.8 |
| CeCl$_3$ | insoluble | − | >50% | <2 | n.o. | n.o. | n.o. |

[a]Condensations were performed with a 100:1 ratio of pyrrole and benzaldehyde at room temperature for 1 h.
[b]Acid solubility was assessed visually.
[c]Color of the reaction mixture: ++++, brown; +++, light brown; ++, yellow; +, pale yellow; −, colorless.
[d]Unreacted benzaldehyde (%) was obtained from TLC using standards of known concentration (lower limit of detection is 0.1%; upper range is 50%).
[e]Relative percentage obtained from GC analysis of the reaction mixture. The amount of benzaldehyde is omitted; hence the values may not sum to 100%.
[f]Refers to "other nonvolatile components" as described in the text.
[g]Not observed.

On the other hand, the Lewis acids examined herein that gave good yields of dipyrromethanes generally gave little tripyrrane 3, substantial amounts of N-confused dipyrromethane 2, and little discoloration of the reaction mixture. It is noteworthy that Yb(OTf)$_3$ and Sc(OTf)$_3$ give significant amounts of N-confused dipyrromethane 2. The general trends observed in the Lewis or Brønsted acid-catalyzed reactions mirrors that observed in our more limited acid studies of TFA and BF$_3$.O(Et)$_2$.[16]

Among all the acids examined, InCl$_3$ and MgBr$_2$ gave the best results considering both the product distribution and color of the reaction mixture. MgBr$_2$ gave less byproducts compared to other Lewis acids, though the reaction rate was slower than that of InCl$_3$, and unreacted benzaldehyde was observed by GC and TLC analysis. We decided to focus on the use of InCl$_3$ as a catalyst for the pyrrole-aldehyde condensation.

B. Concentration Effects on Reaction Rate and Product Distribution. We examined the effects of pyrrole:benzaldehyde ratio (from 25:1 to 400:1) using InCl$_3$ as catalyst in reactions at room temperature. GC analysis was carried out to monitor the progress of the reaction and determine the relative yields of 1, 2, 3, and other components.

The changing ratio of pyrrole:benzaldehyde caused two effects: a change in product composition and a change in reaction rate. The effect of the pyrrole:benzaldehyde ratio on the product distribution is shown in the reaction timecourses in FIG. 4A–D. The reaction with 25 equiv of pyrrole was complete within 10 min (not shown). The reaction with 50 equiv of pyrrole was complete within 30 min but became progressively slower as the amount of pyrrole was increased. With 200 equiv of pyrrole, the reaction required ~2 h to level off, while the reaction with 400 equiv of pyrrole was still proceeding at 3 h and the benzaldehyde was completely consumed only after ~24 h. Thus, an increase in the excess of pyrrole caused a decrease in the reaction rate.

We attribute the decline in rate with increasing excess pyrrole to the dilution of the acid catalyst. The amount of InCl$_3$ was kept constant (0.1 equiv relative to the benzaldehyde) across the varying pyrrole:benzaldehyde ratios. Because pyrrole is the solvent, the acid concentration declined from 54 mM to 3.6 mM (and the benzaldehyde concentration declined from 0.54 M to 0.036 M) as the pyrrole:benzaldehyde ratio increased from 25:1 to 400:1.

Upon increasing the amount of the acid, the reaction time was shortened: with 0.316 or 1 equiv of InCl$_3$, benzaldehyde was consumed within 2 h or 30 min, respectively (FIGS. 4E and F). There was no significant change in the ultimate product distribution of 1, 2, and 3 with alteration of the acid concentration, thereby indicating that approximately the same final product distribution can be achieved at a desired rate by controlling the acid concentration.

Figure 5:
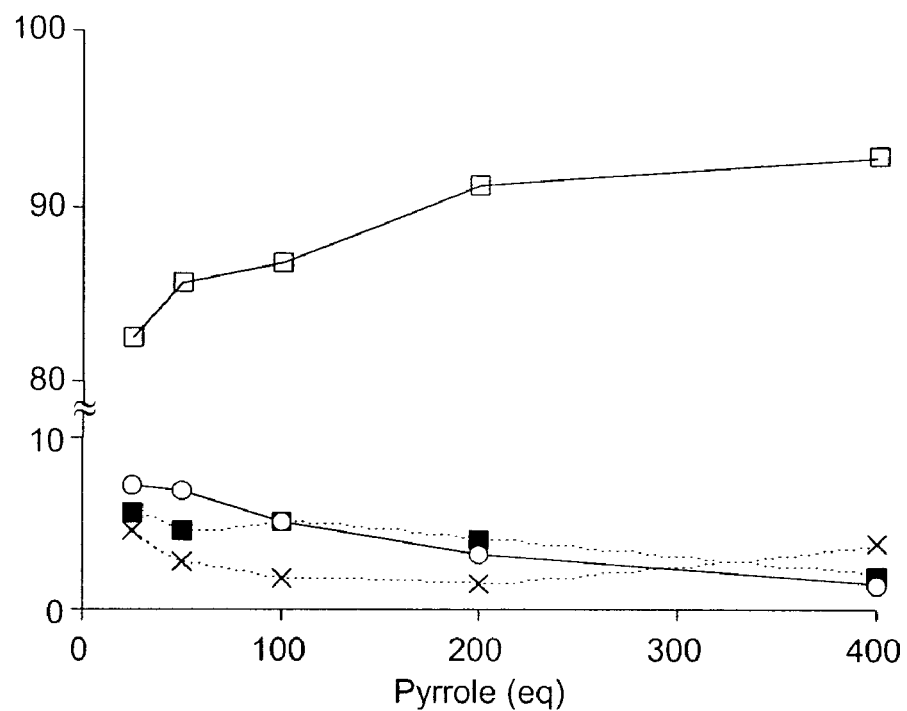
FIG. 5. Expanded display showing the effect of pyrrole: benzaldehyde ratio on the product distribution. The data were obtained by GC analysis for the condensation with $InCl_3$ (0.1 equiv) when the respective reactions leveled off: pyrrole:benzaldehyde=25:1 or 50:1 (30 min); 100:1 (2 h); 200:1 (3 h); or 400:1 (24 h). Legend: 5-phenyldipyrromethane (1, □); N-confused 5-phenyldipyrromethane (2, ■); 5,10-diphenyltripyrrane (3, ○); and the sum of all other volatile components (X).

The ultimate product distribution obtained with varying pyrrole:benzaldehyde and a fixed concentration of InCl$_3$ (0.1 equiv) is shown in FIG. 5. Upon increasing the pyrrole from 25 to 400 equiv, the relative yield of 1 increased steadily from 82.5% to 92.9%, 3 decreased from 7.3% to 1.4%, and 2 declined from 5.6% to 1.9%.

Figure 6:
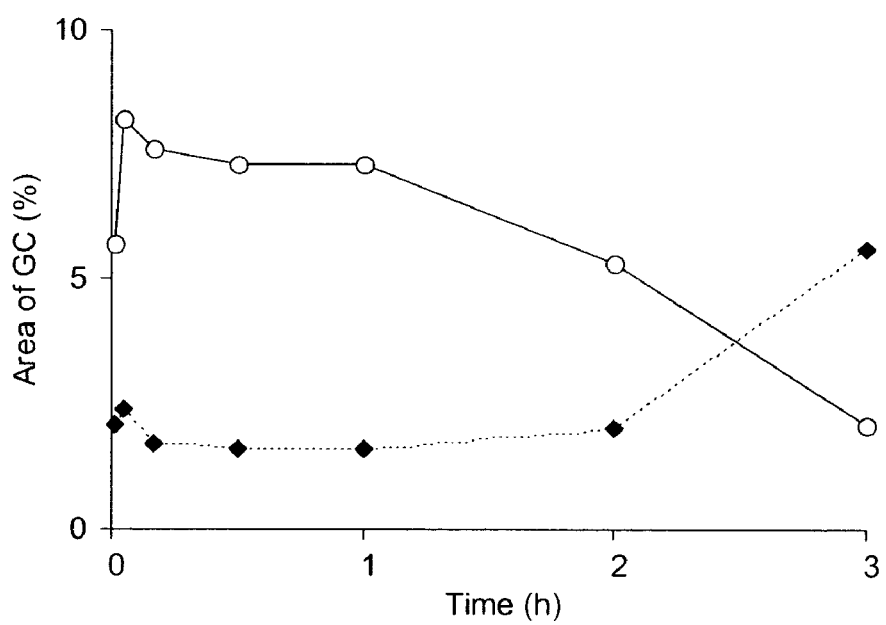
FIG. 6. Relative yield versus time for two byproducts (3, component "A"). The data were obtained by GC analysis from the condensation of pyrrole and benzaldehyde (50:1, 0.1 equiv of $InCl_3$). The early timepoints were at 1 min, 3 min, and 10 min. Legend; 5,10-diphenyltripyrrane (3, ○); unknown peak "A" at $t_R$=12.9 min upon GC analysis (♦).

The apparent clarity of the data masks underlying complexity. Close examination of the reaction timecourses obtained by GC analysis indicated that at least two species exhibit unusual dynamics. The data for tripyrrane 3 from FIG. 4A are plotted at expanded scale in FIG. 6, along with those for component A ($t_R$=12.9 min, m/z=157). The tripyrrane 3 appears in a burst and then declines during the course of the reaction, while component A forms steadily and then increases late in the reaction.

While the mechanistic origins of the dynamics observed for 3 and component A are not known, interpretation of the changes in product distribution over time must take into consideration the changing reaction composition during the course of the condensation. The reaction with 100:1 pyrrole: aldehyde has initial concentrations of 0.14 M for the aldehyde, 14 M for pyrrole, and 0.014 M for the acid. At the end of the reaction, the pyrrole concentration is essentially unchanged while the concentration of water is equal to that of the initial aldehyde (0.14 M) assuming complete reaction. Thus, as the reaction progresses the increasing concentration of water is likely to impact the nature of the acid catalysis. It has been shown that catalysis by lanthanides and related metals entails both Lewis acid catalysis and Brønsted acid catalysis, where the latter is derived by interaction of water with the Lewis acid.[21,33]

III. Workup Method and Purification. We developed a four-step workup procedure that is simple, scalable, and has minimal environmental impact. The four steps are as follows: (1) Quench: to terminate the condensation, excess powdered NaOH (or KOH, LiOH.H$_2$O, or K$_2$CO$_3$) is added and the mixture is stirred for 30 min. (2) Filter: filtration affords recovery of essentially all of the indium material and base. (3) removepyrrole: the filtrate is placed under vacuum, enabling recovery of essentially all of the excess pyrrole (bp 131° C.) in a cold trap. The resulting crude dipyrromethane is often obtained as an oil. The latter is treated with a small volume of hexanes and the hexanes are removed under vacuum, which affords the solid dipyrromethane; this procedure may be repeated 2–3 times to remove residual pyrrole. (4) Recrystallize: recrystallization (aqueous ethanol) affords the dipyrromethane as white crystals.

IV. Comparison of Catalysis by InCl$_3$ or TFA. The 1994 procedure employed TFA as the reaction catalyst.[11,16] For comparison with catalysis by InCl$_3$, a number of studies that parallel those reported in FIGS. 4–6 for InCl$_3$ also were carried out with TFA. The major results are summarized as follows. The TFA catalyzed condensations were faster than that with InCl$_3$. All TFA-catalyzed reactions (0.1 equiv) gave complete consumption of benzaldehyde within 30 min and the reaction composition remained unchanged thereafter. Regardless, the two dominant effects observed with InCl$_3$ also were observed with TFA catalysis: (1) An increase in the pyrrole:benzaldehyde ratio caused the reaction rate to decrease. (2) Upon increasing the pyrrole:benzaldehyde ratio from 25 to 400, the yield of 1 increased from 65 to 93%, the yield of 3 decreased, and the yield of 2 remained constant (>2%).

One distinction between the two catalysts was observed in the purification process. The reaction mixture obtained upon TFA catalysis with a 200:1 or 400:1 ratio of pyrrole: benzaldehyde was worked up without use of aqueous/ organic extraction, distillation, or chromatography as employed previously. After neutralization of the acid and removal of the pyrrole, crystallization of the crude product gave a dark brown solid. The discoloration of the product could not be remedied by repeated crystallization, requiring instead treatment with charcoal in hot ethanol (or, on a small scale, silica pad filtration) followed by recrystallization.

V. Scope of Application.

General Method. The refined synthesis conditions using InCl$_3$ were applied to the series of aldehydes shown in Scheme 2. We chose a pyrrole:benzaldehyde ratio of 100:1 as a compromise among three factors affected by an increasing pyrrole:benzaldehyde ratio: (i) the increased yield of dipyrromethane, (ii) the decreased rate of reaction, and (iii)

the necessity to handle a large amount of pyrrole relative to that of the product. Each reaction was performed at room temperature with 50 mmol of aldehyde and 0.1 equiv of InCl$_3$. The progress of the reactions was monitored by TLC and GC. The workup procedure entailed the four-step procedure outlined above. For comparison, the same reactions were carried out with 20 mmol of the aldehyde and purification was carried out by column chromatography.

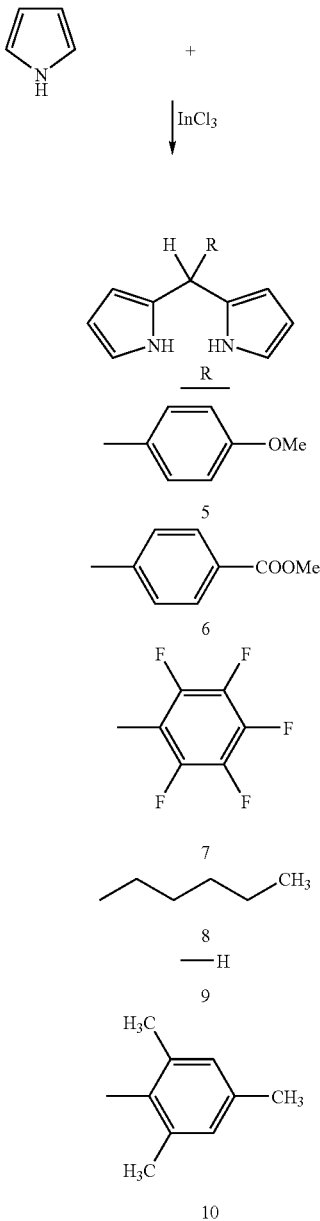

The results for dipyrromethanes 1 and 5–9 are summarized in Table 2. The standard reaction conditions and workup procedure generally gave good results with each of the aldehydes. Each dipyrromethane gave a relative GC purity of >90%. Minor modifications were made for dipyrromethanes 6 and 8. In the case of 6 a small amount (7%) of transesterification product was obtained when aqueous ethanol was employed for recrystallization. Hence, aqueous methanol (10:1) was used for the recrystallization. Dipyrromethane 8, an oil, was obtained by column chromatography. More extensive changes were made for the reactions with paraformaldehyde and mesitaldehyde.

TABLE 2

Scope of application of the refined synthesis method.[a]

| Dipyrromethane | Yield (Purity)[b] | | |
|---|---|---|---|
| | Crystallization | | |
| | 1$^{st}$ crystallization[c] | 2$^{nd}$ crystallization | Chromatography |
| 1 | 71% (96.7%) | | 82% (>99%) |
| 5 | 63% (92.0%) | 43% (97.0%) | 62% (>99%) |
| 6 | 75% (97.0%) | | 75% (>99%) |
| 7 | 79% (>99%) | | 80% (98.0%) |
| 8[d] | n.a.[e] | n.a. | 62% (94.3%) |
| 9[f] | 45% (94.6%) | | 63% (>99%) |

[a] Condensations were performed with a 100:1 ratio of pyrrole:aldehyde with 0.1 equiv of InCl$_3$ at room temperature for 1.5 h unless specified.
[b] Relative purity (%) based on GC peak areas is shown in parentheses. The workup procedure involves quenching with powdered NaOH, filtration, removal of pyrrole and entrainment with hexanes unless specified, followed by crystallization or chromatography.
[c] May include a 1$^{st}$ and 2$^{nd}$ crop of crystals.
[d] Obtained as an oil.
[e] Not applicable.
[f] After reaction at 55° C. for 2.5 h, the reaction mixture was extracted with hexanes/ethyl acetate prior to crystallization.

Special Cases. A. Paraformaldehyde. Paraformaldehyde was relatively insoluble in neat pyrrole. The heterogeneous reaction mixture was heated at 50–55° C. for 2.5 h. Pyrrole was removed, then dipyrromethane (9) was extracted with hexanes/ethyl acetate (4:1). Evaporation of the solvent followed by crystallization [methanol/water (4:1)] afforded 9 in 45% yield (94.6% purity by GC), to be compared with 63% yield (>99% purity by GC) by chromatography.

B. Mesitaldehyde. The reaction of mesitaldehyde with pyrrole in the presence of 0.1 equiv of InCl$_3$ proceeded very slowly. A survey of acid catalysts and acid concentration (0.1 to 1.0 equiv) was performed for the reaction with a 100:1 ratio of pyrrole:benzaldehyde. The conditions that gave the best result for each acid are summarized in Table 3. The GC traces generally mirrored those obtained for benzaldehyde, including the appearance of a series of peaks attributed to isomeric tripyrranes. We examined the effects of different acids and different concentrations of acids in the reaction of mesitaldehyde with excess pyrrole (data not shown). To examine the effect of increasing the amount of InCl$_3$ with respect to the aldehyde, reactions were carried out (100:1 ratio of pyrrole:mesitaldehyde) with 0.1, 0.3, or 0.5 equiv of InCl$_3$. The GC trace indicated the presence of a considerable amount of unreacted mesitaldehyde though the relative percentage decreased with an increasing amount of InCl$_3$ (data not shown). A separate experiment with a 400:1 ratio of pyrrole:mesitaldehyde in the presence of 0.3 equiv of InCl$_3$ also exhibited a considerable amount of unreacted mesitaldehyde upon GC analysis. Use of excess catalyst also did not improve the results. Owing to the slower reaction, we increased the temperature to 60° C. for the reaction with a 100:1 ratio of pyrrole:mesitaldehyde. Upon reaction with 0.3 equiv of InCl$_3$ at 60° C., <10% of mesitaldehyde remained.

To further improve the yield of 5-mesityldipyrromethane, the effects of other catalysts were also examined. The use of 0.1 equiv of TFA with a 100:1 ratio of pyrrole:mesitaldehyde resulted in the complete consumption of mesitaldehyde in 1 h. Attempts to isolate the product with the standard workup procedure afforded a brown solid in low yield (25%). With 0.1 equiv of malonic acid under the same conditions, 37.5% of unreacted mesitaldehyde remained. Since the reaction mixture turned dark upon adding malonic acid, the effects of a larger amount of the catalyst were not studied. The utility of Sc(OTf)$_3$ was also studied). In each reaction with Sc(OTf)$_3$, the amount of N-confused 5-mesityldipyrromethane was substantially larger than that upon reaction with an equal amount of InCl$_3$.

In the survey of various acid catalysts for the pyrrole-benzaldehyde condensation, MgBr$_2$ gave a good yield of 5-phenyldipyrromethane with little N-confused 5-phenyldipyrromethane and 5,10-diphenyltripyrrane. This observation prompted us to study the effect of MgBr$_2$ on the pyrrole-mesitaldehyde condensation. Four reactions were carried out with 0.1, 0.3, 0.5 or 1.0 equiv of MgBr$_2$ using a 100:1 ratio of pyrrole:mesitaldehyde at room temperature. For the reaction with 0.5 equiv of MgBr$_2$, GC analysis showed 82.9% of 5-mesityldipyrromethane and 0.9% of unreacted mesitaldehyde. Among the acids surveyed, the use of 0.5 equiv of MgBr$_2$ appeared superior for the synthesis of 5-mesityldipyrromethane.

results overall were observed with MgBr$_2$, which also gave the least discolored reaction mixture. The isolated yield was 53% (93.7% purity), nearly double that obtained previously.

VI. Scale-up.

A large-scale synthesis of 5-phenyldipyrromethane (1) was carried out using benzaldehyde (79.8 g) and 100 equiv of pyrrole (5.20 L) with catalysis by InCl$_3$ (16.7 g) and mechanical stirring for 1.5 h at room temperature. The reaction mixture remained essentially at room temperature without application of external temperature control. The reaction was quenched by adding NaOH and the mixture was filtered and washed with pyrrole (0.35 L). The mixture was concentrated and pyrrole was recovered (5.30 L). The crude dipyrromethane solidified upon treatment with hexanes and was recrystallized from ethanol/water (4:1) affording four crops of crystals. The third and fourth crop were combined and recrystallized. The three samples each gave satisfactory elemental analyses yet the GC analyses indicated purities of 94.8%, 92.3%, and 94.0%. The typical GC data (crop 2) indicated the relative amounts of 92.3% (1), 6.3% (2), 0.6% (3) and 0.8% (other volatile components). $^1$H

TABLE 3

Refined acid catalysis conditions for 5-mesityldipyrromethane (10) synthesis.[a]

| Catalyst | Conditions | Relative Amounts (%) by GC | | | | | Yield (Purity)[c] | |
| --- | --- | --- | --- | --- | --- | --- | --- | --- |
| | | MsCHO[b] | 10 | 11[c] | 12[d] | Other[e] | Crystallization | Chromatography |
| TFA | 0.1 equiv, rt, 1.5 h | 0.2 | 77.1 | 2.1 | 12.5 | 8.1 | 25% (90.0%) | 27%[f] |
| Malonic acid | 0.1 equiv, rt, 3 h | 37.5 | 52.7 | 1.1 | 4.2 | 4.5 | n.a.[g] | n.a. |
| InCl$_3$ | 0.3 equiv, 60° C., 5 h | 7.6 | 67.9 | 18.3 | 3.3 | 2.9 | 49% (85.7%)[h] | 56% (82.0%) |
| Sc(OTf)$_3$ | 0.3 equiv, rt, 4 h | 0.8 | 52.7 | 30.2 | 1.6 | 14.7 | n.a. | na. |
| MgBr$_2$ | 0.5 equiv, rt, 1.5 h | 0.9 | 82.9 | 3.5 | 4.8 | 7.9 | 53% (93.0%) | 65% (92.7%) |

[a]Condensations were performed with a 100:1 ratio of pyrrole:mesitaldehyde.
[b]Mesitaldehyde.
[c]N-confused 5-mesityldipyrromethane.
[d]5,10-Dimesityltripyrrane.
[e]Refers to "other nonvolatile components" as described in the text.
[f]Obtained by Kugelrohr distillation followed by crystallization using the reported method.[14]
[g]Not applicable.
[h]Yield of 32% (88.0%) in the 1$^{st}$ crop, 17% (81.2%) in the 2$^{nd}$ crop.

In Summary, GC examination showed generally high relative yields of 5-mesityldipyrromethane (10) with each of the acids. However, the Brønsted acid catalysts gave dark brown-black reaction mixtures while those with Lewis acid catalysts were discolored to a lesser extent. The discoloration of the reaction mixture—while difficult to quantify and stemming from products that are difficult to analyze—is the likely cause of the yield of isolated dipyrromethane falling short of that expected based on GC analysis. A case in point is provided by the reaction obtained with TFA: the relative percentage of 10 is 77% (by GC analysis) while the isolated yield is 27%.[16] From these studies, we focused on the Lewis acid catalysts. The product distribution obtained with Sc(OTf)$_3$ contained a significant amount of the N-confused dipyrromethane 11. The reaction with InCl$_3$ at 60° C. afforded a relatively good yield of the dipyrromethane 10, but crystallization to high purity proved difficult. The best NMR analysis showed a corresponding ratio of 1:2:3 while other components were not observed. Altogether, 116 g of 1 (70% yield, 94.2% purity by GC) was obtained. Distillation of the recovered pyrrole afforded 4.92 L of pyrrole (90% final recovery).

VII. Material Recovery and Reuse.

Filtration of the reaction mixture affords recovery of the indium employed as catalyst in conjunction with the excess base for neutralization. We have not attempted to regenerate the indium catalyst. However, the pyrrole has been recycled numerous times. One caveat is that some aldehydes (e.g., hexanal, bp 128° C.) may have bp nearly identical with that of pyrrole (bp 131° C.). In such cases, the recovered pyrrole should be used exclusively for subsequent reaction with the same aldehyde to avoid any possibility of contamination by residual unreacted aldehyde.

Conclusion. The one-flask solventless reaction of an aldehyde with excess pyrrole provides a simple means of preparing the corresponding dipyrromethane. A wide variety of Brønsted or Lewis acids can be employed as catalyst. The Brønsted acids that afford product also give a dark reaction mixture, while the Lewis acids give less discoloration. Excellent results were obtained with $InCl_3$ (for benzaldehyde and other aryl aldehydes) and $MgBr_2$ (for mesitaldehyde). The workup procedure entails quenching with NaOH, filtration, removal of pyrrole, and crystallization. The simplicity of this procedure (no aqueous/organic extraction, distillation, or chromatography) minimizes waste and enables scalability. The absence of any reaction solvent other than pyrrole enables facile recovery of the excess pyrrole from the crude reaction mixture; the recovered pyrrole can be reused. Indeed, the reaction of 0.75 mmol of benzaldehyde in 5.2 L of pyrrole gave 116 g of 5-phenyldipyrromethane and recovery of 90% of the excess pyrrole in a form suitable for reuse. Characterization of the purity of dipyrromethanes is best accomplished using a combination of analytical techniques, including gas chromatography. Given that the N-confused dipyrromethane(s) and the tripyrrane(s) are dominant byproducts of the reaction, and the former while the latter is an isomer of the dipyrromethane, a satisfactory elemental analysis is a necessary but insufficient criterion of purity.

References.
(1) (a) A. Treibs et al, *Liebigs Ann. Chem.* 1968, 718, 183. (b) R. Chong et al., *Aust. J. Chem.* 1969, 22, 229. (c) P. Clezy et al., *Aust. J. Chem.* 1969, 22, 239. (d) R. Wilson et al., *J. Org. Chem.* 1987, 52, 2699. (e) D. Wallace et al., *J. Org. Chem.* 1993, 58, 7245. (f) J. Setsune et al., *J. Chem. Soc., Chem. Commun.* 1994, 657. (g) J. Setsune et al., *Tetrahedron* 1998, 54, 1407. (h) H. Volz et al., *Angew. Chem. Int. Ed. Engl.* 1997, 36, 1442. (i) V. Lin et al., *J. Inorg. Synth.* 2002, 33, 55.
(2) J. Nagarkatti and K. Ashley, *Synthesis* 1974, 186.
(3) D. Hammel et al., *Adv. Mater.* 1992, 4, 737.
(4) S. Vigmond et al., *Anal. Chem.* 1992, 64, 2763.
(5) S. Vigmond et al., *Tetrahedron Lett.* 1994, 35, 2455.
(6) (a) G. Casiraghi et al., *J. Org. Chem.* 1994, 59, 1801. (b) M. Cornia et al., *J. Org. Chem.* 1995, 60, 4964. Also see: G. Casiraghi et al., *Tetrahedron* 1992, 48, 5619.
(7) T. Mizutani et al., *J. Am. Chem. Soc.* 1994, 116, 4240.
(8) (a) R. Boyle et al., *Synlett* 1994, 939. (b) R. Boyle et al., *Tetrahedron Lett.* 1994, 35, 5377.
(9) (a) H. Staab et al., *A. Chem. Ber.* 1994, 127, 223. (b) G. Shipps et al., *Tetrahedron Lett.* 1994, 35, 6823. (c) T. Carell, Ph.D. thesis, Ruprecht-Karls-Universität Heidelberg, 1993.
(10) (a) T. Wijesekera, *Can. J. Chem.* 1996, 74, 1868. (b) N. Nishino et al., *J. Org. Chem.* 1996, 61, 7534.
(11) C. Lee and J. Lindsey, *Tetrahedron* 1994, 50, 11427.
(12) D. Gryko and J. Lindsey, *J. Org. Chem.* 2000, 65, 2249.
(13) C. Brückner et al. *Chem. Commun.* 1997, 1689.
(14) R. Boyle et al., *Org. Synth.* 1998, 76, 287.
(15) C. Brückner et al., *J. Porphyrins Phthalocyanines* 1998, 2, 455.
(16) B. Littler et al. *J. Org. Chem.* 1999, 64, 1391.
(17) C. Brückner et al., *Can. J. Chem.* 1996, 74, 2182.
(18) G. Geier, et al., *Org. Lett.* 2000, 2, 1745.
(19) G. Geier et al., *J. Porphyrins Phthalocyanines* 2002, 6, 159.
(20) G. Geier et al., *J. Porphyrins Phthalocyanines* 2001, 5, 810.
(21) M. Speckbacher et al., *Inorg. Chem.* 2003, 42, in press.
(22) (a) S. Babu, *Synlett* 2002, 531. (b) S. Kobayashi et al., *Chem. Rev.* 2002, 102, 2227.
(23) (a) R. Loewe et al., *J. Mater. Chem.* 2002, 12, 3438. (b) L. Yu et al., *Inorg. Chem.* submitted.
(24) R. Naik et al., *Tetrahedron* 2003, 59, 2207.
(25) A. Sobral et al., *Tetrahedron Lett.* 2003, 44, 3971.
(26) W.-S. Cho et al., *Bull. Korean Chem. Soc.* 1998, 19, 314.
(27) (a) T. Dubé et al., *Organometallics* 2000, 19, 3716. (b) C. Bucher et al., *J. Am. Chem. Soc.* 2001, 123, 2099. (c) N. Arumugam et al., *Bull. Korean Chem. Soc.* 2001, 22, 932. (d) S. Depraetere et al., *Tetrahedron Lett.* 2003, 44, 345.
(28) P. Beer et al., *Dalton Trans.* 2003, 603.
(29) J.-W. Ka, *Tetrahedron Lett.* 2000, 41, 4609.
(30) F. Li et al., *Tetrahedron* 1997, 53, 12339.
(31) C. Hill et al., *J. Chem. Soc., Chem. Commun.* 1985, 1228.
(32) J. Lindsey, et al., *J. Org. Chem.* 1989, 54, 828.
(33) A. Barrett et al., *J. Chem. Soc., Perkin Trans. 1* 1999, 873.
(34) C. Brückner et al., *Inorg. Chim. Acta* 1997, 263, 279.
(35) H. Wagenknecht et al., *Helv. Chim. Acta* 1998, 81, 1506.
(36) Q. Wang et al., *Synlett* 1995, 1267.

The foregoing is illustrative of the present invention, and is not to be construed as limiting thereof. The invention is defined by the following claims, with equivalents of the claims to be included therein.

That which is claimed is:
1. A non-aqueous method of making a dipyrromethane, comprising the steps of:
 (a) providing a non-aqueous reaction system consisting essentially of (i) an aldehyde or acetal, (ii) excess pyrrole and (iii) a catalyst;
 (b) reacting said aldehyde or acetal with said pyrrole in said non-aqueous reaction system to form said dipyrromethane therein;
 (c) quenching said non-aqueous reaction system by adding a base thereto without adding an organic solvent thereto;
 (d) separating said catalyst from said non-aqueous reaction system, wherein said separating step is carried out by gravity or filtration; and then
 (e) separating said pyrrole from said non-aqueous reaction system to produce said dipyrromethane as a residual.
2. The method of claim 1, further comprising the step of:
 (f) crystallizing said dipyrromethane.
3. The method of claim 1, wherein said aldehyde has the general formula RC(=O)H, wherein R is H, alkyl or aryl.
4. The method of claim 1, wherein said aldehyde is selected from the group consisting of formaldehyde, paraformaldehyde, acetaldehyde, propionaldehyde, n-butyraldehyde, benzaldehyde, p-nitrobenzaldehyde, p-tolualdehyde, salicylaldehyde, phenylacetaldehyde, α-methylvaleraldehyde, β-methylvaleraldehyde, γ-methylvaleraldehyde, 4-pyridine carboxaldehyde, pentafluorobenzaldehyde, 4-ethynylbenzaldehyde, 4-[2-(triisopropylsilyl)ethynyl]benzaldehyde, 4-[3-methyl-3-hydroxy-but-1-ynyl)benzaldehyde, 4-(S-acetylthiomethyl)benzaldehyde, 4-(Se-acetyl-selenomethyl)benzaldehyde, 4-(hydroxymethyl) benzaldehyde, 4-vinylbenzaldehyde, 4-allylbenzaldehyde, 4-cyanobenzaldehyde, 4-iodobenzaldehyde, 4-(bromomethyl)benzaldehyde, 4-(2-bromoethyl)benzaldehyde, 4-(1,3-dithiolan-2-yl)benzaldehyde, 4-(1,3-dithian-2-yl)benzaldehyde, 4-(4,4,5,5-tetramethyl-1,3,2-dioxaborolan-2-yl) benzaldehyde, 4-(acetoxymethyl)benzaldehyde, 4-[2-

(trimethylsilyl)ethoxy-carbonyl]benzaldehyde, 4-methoxycarbonylbenzaldehyde, 5-[4-(di-tert-butyloxyphosphoryl)benzaldehyde, 5-[4-(diethoxyphosphoryl)benzaldehyde, 5-[4-(di-tert-butyloxyphosphorylmethyl)benzaldehyde, 5-[4-(diethoxyphosphorylmethyl)benzaldehyde, 1,1,1-tris[4-(diethoxyphosphorylmethyl)phenyl]-1-(4-formylphenyl)methane, 1,1,1-tris[4-(S-acetylthiomethyl)phenyl]-1-(4-formylphenyl)methane, 3-(S-acetylthiomethyl)benzaldehyde, 3,5-diethynylbenzaldehyde, 3,5-bis[2-(triisopropyl-silyl)ethynyl]benzaldehyde, 4-(5,10,15-tri-p-tolylporphinatozinc(II)-20-yl)benzaldehyde, 4-(5,10,15-tri-p-tolylporphin-20-yl)benzaldehyde, 4-(dipyrrin-5-yl)benzaldehyde, 4-[1,9-bis(4-methylbenzoyl)dipyrromethan-5-yl]benzaldehyde, 4-ferrocenylbenzaldehyde, propargyl aldehyde, bromomethylpropargyl aldehyde, chloromethylpropargyl aldehyde, S-acetylthiomethylpropargyl aldehyde, 4-(hydroxymethyl)phenylpropargyl aldehyde, hydroxyacetaldehyde, and pyruvic aldehyde.

5. The method of claim 1, wherein said acetal has the general formula RC(—OR')(—OR")H, wherein R, R' and R' are alkyl or aryl.

6. The method of claim 1, wherein said catalyst is a Bronsted acid.

7. The method of claim 6, wherein said Bronsted acid is selected from the group consisting of trifluoroacetic acid, trichloroacetic acid, oxalic acid, taurine, malonic acid, formic acid, acetic acid, and $NH_4Cl$.

8. The method of claim 1, wherein said catalyst is a Lewis acid.

9. The method of claim 8, wherein said Lewis acid is selected from the group consisting of $InCl_3$, $Sc(OTf)_3$, $MgBr_2$, $CeCl_3$ and $LnX_3$ wherein Ln is a lanthanide metal and X is halo or OTf.

10. The method of claim 1, wherein said separating step (c) is carried out by filtering.

11. The method of claim 1, wherein said separating step (c) is carried out by centrifugation.

12. The method of claim 1, wherein said separating step (c) is carried out by settling.

13. The method of claim 1, wherein said catalyst is a Lewis acid catalyst, wherein said quenching step precipitates said catalyst from said reaction system, and wherein said separating step (d) is carried out by filtering or gravity.

14. The method of claim 1, further comprising the step of synthesizing a porphyrinic macrocyle from said dipyrromethane.

15. The method of claim 1, further comprising the step of synthesizing a dipyrrin from said dipyrromethane.

16. The method of claim 1, further comprising the step of reacting said dipyrromethane with an oxidant and a metal salt to produce a bis(dipyrrinato)metal complex.

17. The method of claim 16, wherein said oxidant is selected from the group consisting of DDQ, o-chloranil, and p-chloranil.

18. The method of claim 16, wherein said metal salt is selected from the group consisting of zinc, palladium, copper, nickel, and cobalt salts.

19. The method of claim 16, further comprising the steps of coupling a porphyrinic macrocycle to said bis(dipyrrinato)metal complex to form a reaction product; and then treating said reaction product with a thiol reagent to disassemble said reaction product and form a dipyrrin-substituted porphyrinic macrocycle.

20. The method of claim 19, wherein said thiol reagent is selected from the group consisting of dithiothreitol, 2-mercaptoethanol, butanethiol, and dithioerythritol.

21. The method of claim 16, further comprising the step of reacting said bis(dipyrrinato)metal complex with a thiol reagent under neutral conditions to disassemble said bis(dipyrrinato)metal complex into separate dipyrrin groups.

22. A method according to claim 1, further comprising the step of reacting a dipyrrin-carboxaldehyde with said dipyrromethane in the presence of an acid catalyst to produce said trans-(dipyrrin)$_2$-porphyrinic macrocycle.

23. The method of claim 22, wherein said reacting step is carried out at a temperature of from 0 to 100° C.

24. The method of claim 22, wherein said reacting step is carried out in a solvent selected from the group consisting of dichloromethane, tetrahydrofuran, toluene, chloroform, and mixtures thereof.

* * * * *